United States Patent
Ichim

(10) Patent No.: US 10,088,485 B2
(45) Date of Patent: *Oct. 2, 2018

(54) METHODS OF SCREENING COMPOUNDS THAT CAN MODULATE NR2F6 BY DISPLACEMENT OF A REFERENCE LIGAND

(71) Applicant: Regen BioPharma, Inc, La Mesa, CA (US)

(72) Inventor: Christine Victoria Ichim, Spring Valley, CA (US)

(73) Assignee: Regen Biopharma, La Mesa, CA (US)

( * ) Notice: Subject to any disclaimer, the term of this patent is extended or adjusted under 35 U.S.C. 154(b) by 338 days.

This patent is subject to a terminal disclaimer.

(21) Appl. No.: 14/852,623

(22) Filed: Sep. 13, 2015

(65) Prior Publication Data

US 2016/0025746 A1    Jan. 28, 2016

Related U.S. Application Data

(63) Continuation-in-part of application No. 14/571,262, filed on Dec. 15, 2014, now abandoned, which is a continuation-in-part of application No. 13/652,395, filed on Oct. 15, 2012, now Pat. No. 9,091,696, which is a continuation-in-part of application No. 12/619,290, filed on Nov. 16, 2009, now abandoned.

(60) Provisional application No. 61/114,764, filed on Nov. 14, 2008.

(51) Int. Cl.
| | | |
|---|---|---|
| *A61K 38/00* | (2006.01) | |
| *G01N 33/68* | (2006.01) | |
| *A61K 31/00* | (2006.01) | |
| *A61K 31/7088* | (2006.01) | |
| *G01N 33/574* | (2006.01) | |

(52) U.S. Cl.
CPC ......... *G01N 33/6875* (2013.01); *A61K 31/00* (2013.01); *A61K 31/7088* (2013.01); *G01N 33/57426* (2013.01); *G01N 33/6872* (2013.01); *G01N 2333/70567* (2013.01); *G01N 2500/04* (2013.01); *G01N 2800/22* (2013.01)

(58) Field of Classification Search
None
See application file for complete search history.

*Primary Examiner* — Michail A Belyavskyi
(74) *Attorney, Agent, or Firm* — Baumgartner Patent Law; Marc Baumgartner

(57) ABSTRACT

The current invention discloses compositions of matter, protocols and methods of screening test compounds to identifying agonists and antagonists of the orphan nuclear receptor NR2F6 by measuring the ability of a test compound to occupy the active site of NR2F6, in the presence of a reference compound.

16 Claims, 8 Drawing Sheets
Specification includes a Sequence Listing.

pSiren shNR2F6.1

METHODS OF SCREENING COMPOUNDS THAT CAN MODULATE NR2F6 BY DISPLACEMENT OF A REFERENCE LIGAND

CROSS-REFERENCE TO RELATED APPLICATIONS

This application claims priority to and is a continuation-in-part to pending U.S. application Ser. No. 14/571,262, filed Dec. 15, 2014, now abandoned, which claims priority to and is a continuation-in-part to U.S. application Ser. No. 13/652,395 filed Oct. 15, 2012, now U.S. Pat. No. 9,091,696, which claims priority to and is a continuation-in-part to Non-Provisional U.S. application Ser. No. 12/619,290, filed Nov. 16, 2009, now abandoned, which claims the benefit under 35 USC § 119(e) of U.S. provisional application No. 61/114,764 filed Nov. 14, 2008, each of which is hereby expressly incorporated by reference in their entirety.

SEQUENCE LISTING

The instant application contains a Sequence Listing which has been submitted electronically in ASCII format and is hereby incorporated by reference in its entirety. Said ASCII copy, created on Oct. 8, 2015, is named REGENCHRISTINE-CIP7_SL.txt and is 19,327 bytes in size.

FIELD OF THE INVENTION

The invention presents a method of screening test compounds to identifying agonists and antagonists of the orphan nuclear receptor NR2F6 by measuring the ability of a test compound to occupy the active site of NR2F6, in the presence of a reference compound.

BACKGROUND

NR2F6, known also as EAR-2, is an orphan nuclear receptor that was cloned in a search for homologues of the retroviral oncogene v-erbA using low stringency hybridization (see Miyajima, N., et al., (Identification of two novel members of erbA superfamily by molecular cloning: the gene products of the two are highly related to each other. Nucleic Acids Res, 16(23): p. 11057-74. 1988)). EAR-2 is a member of the chicken ovalbumin upstream promoter (COUP) family of nuclear receptors. The COUPs function in vitro as transcriptional repressors, antagonizing the activation ability of a wide range of nuclear receptors that play prominent roles in differentiation. Accordingly, aberrant expression of COUP-TFI inhibits retinoid-induced epithelial and neuronal differentiation in vitro (Please see Kyakumoto, S., M. Ota, and N. Sato (Inhibition of retinoic acid-inducible transcription by COUP-TFI in human salivary gland adenocarcinoma cell line HSG. Biochem Cell Biol, 77(6): p. 515-26. 1999), Neuman, K., et al., (Orphan receptor COUP-TF I antagonizes retinoic acid-induced neuronal differentiation. J Neurosci Res, 41(1): p. 39-48. 1995) and Adam, F., et al., (COUP-TFI (chicken ovalbumin upstream promoter-transcription factor I) regulates cell migration and axogenesis in differentiating P19 embryonal carcinoma cells. Mol Endocrinol, 14(12): p. 1918-33. 2000)). The roles of COUP-TFI and COUP-TFII in mammalian development have been studied by targeted deletion in the mouse. COUP-TFI deficient mice exhibit numerous defects in axonal development, including failure of development of the nucleus of the 9th cranial nerve. COUP-TFII deletion causes widespread defects in angiogenesis and cardiac development, leading to embryonic lethality in mid-gestation. Seven-up (svp), the *Drosophila* COUP family homologue, is also important in embryonic development; with null mutations of seven-up being embryonic lethal. svp is involved in decisions of cell fate determination during the development of the photoreceptors in the ommatidium of the eye and regulates proliferation during the development of the malpighian tubules by regulating the expression of cell cycle regulators. Improvements are needed in the field of screening test compounds to identify agonists and antagonists of the orphan nuclear receptor NR2F6.

SUMMARY OF THE INVENTION

The present invention provides a method of identifying compounds for the treatment of diseases or disorders modulated by NR2F6, comprising the step of (i) Expressing in a cellular or cell-free system proteins encoded by one or more recombinant DNA vectors that comprises a ligand binding assay system, having a portion of the cDNA with SEQ ID NO:1. (ii) Selecting a molecule that can be used as a known ligand, that has been predetermined to bind to the recombinant protein generated by the DNA vectors used in step (i) to generate an amino acid sequence of at least 75% sequence identity to a portion of the amino acid sequence of SEQ ID NO:3 (iii). Labeling the known ligand using radioactive or non-radioactive methods; or leaving the known ligand unlabeled if detection is performed using the label-free variant of the ligand binding assay. (iv) Measure the ability of the known ligand to bind to the recombinant protein expressed in step (i). (v) Contacting the ligand binding assay with a candidate test compound. (vi) Measure the ability of the known ligand to bind to the recombinant protein expressed in step (i) while in the presence of test compound. (vii) Determine the ability of the candidate test compound to bind to the recombinant protein expressed in step (i) by comparing the binding of the known ligand without test compound to the binding of the known ligand after addition of the test compound.

Recombinant DNA vectors may be expressed in a system where recombinant protein is generated with the vectors and isolated from *Escherichia coli*.

It is important that the molecule used as the known ligand be predetermined to bind to sites on NR2F6 that regulate its function. One active such site is the ligand-binding domain of NR2F6, however it is also possible to use this assay to assess binding to allosteric site on recombinant or native NR2F6 protein.

We have found that the molecule troglitazone binds to NR2F6, and have devised an assay using troglitazone as well as its related family member, thiazolidinedione, and have provided a list of many other chemicals that may be suitable known ligands.

There are a number of ways to detect binding, these include labeling the known ligand with enzymatic, fluorescence, or radioactive detection methods, labeling the protein with enzymatic, fluorescence, or radioactive detection methods, or both.

The following are methods that can be used in the assay system if detection using fluorescence is preferred: fluorescence polarization (FP), fluorescence resonance energy transfer (FRET), fluorescence anisotropy, fluorescence correlation spectroscopy, or time-resolved fluorescence. However, if detection using radiolabelling is preferred one can use a number of isotopes including 3H and 125I to label the known ligand and use a scintillation proximity assay (SPA)

format to detect binding, radioligand binding filtration assay, ScreenReady™ type of assay, FlashPlate ligand binding assay formats or other suitable detection format.

Alternatively, binding can be detected using a label free format. This method often involves measuring the ability of the test ligand to bind recombinant protein using a non-radioactive way that measures the change in the angle of polarized light to reflect from a surface on to which ligand or protein has been immobilized. The following are methods that can be used in the assay system if detection is preferred using a label free format: Surface plasmon resonance (SPR), Plasmon-waveguide resonance (PWR), SPR imaging for affinity-based biosensors, Whispering gallery microresonator (WGM), Resonant waveguide grating (RWG), Biolayer Interferometry Biosensor (BIB).

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Figure 1:
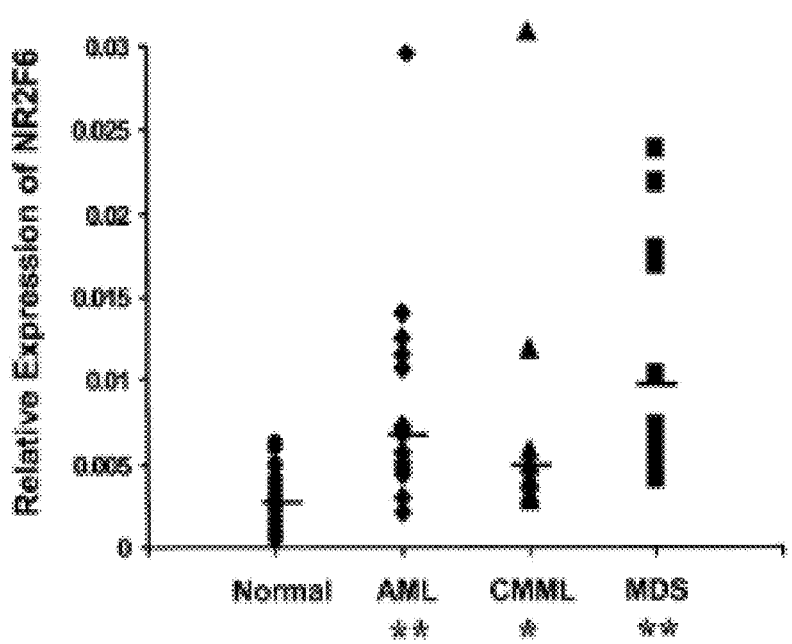
FIG. 1 shows that NR2F6 is highly expressed in both long and short term haematopoietic stem cells and that expression of NR2F6 in bone marrow from patients with acute myelogenous leukemia (AML), chronic myelomonocytic leukemia (CMML) and myelodysplastic syndrome (MDS) is greater compared to control. * denotes p<0.05 and ** denotes p<0.01 relative to normal (ANOVA & Tukey post-hoc test).
Figure 2:
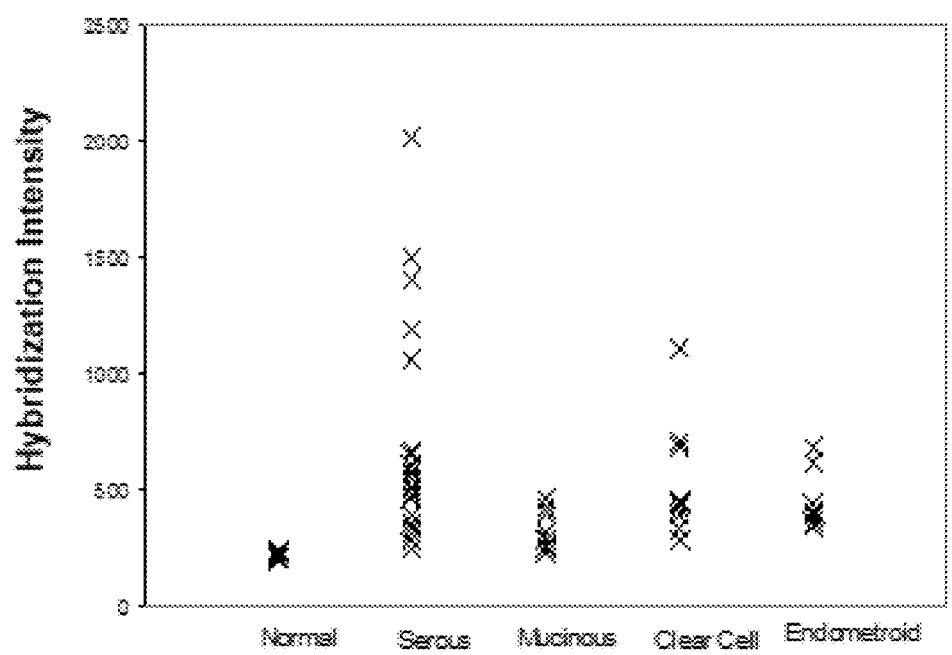
FIG. 2 shows that expression of NR2F6 is greater in all types of ovarian cancer as determined by in silico analysis.
Figure 3:
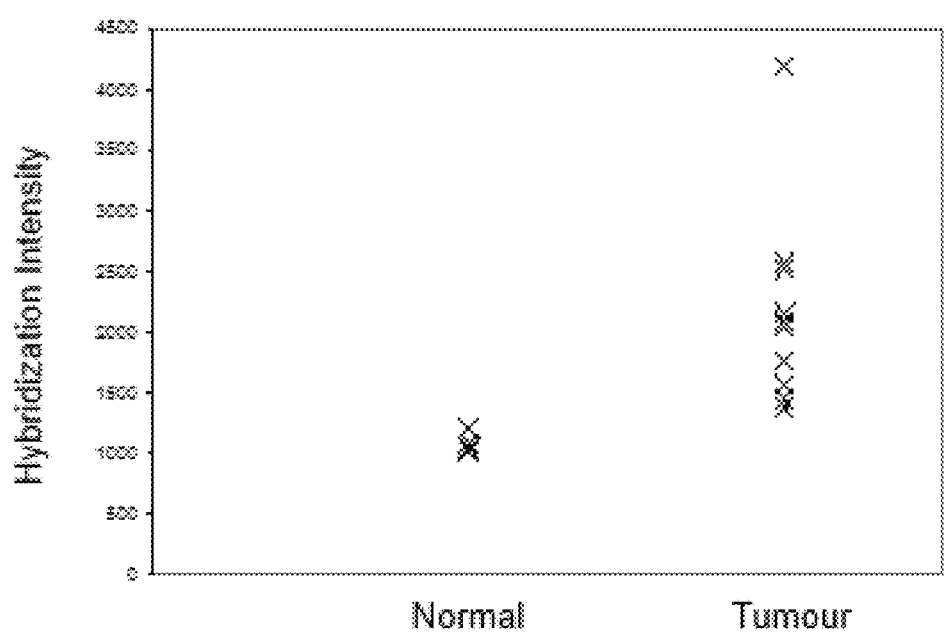
FIG. 3 shows that expression of NR2F6 is greater in endometrial cancer as determined by in silico analysis.
Figure 4:
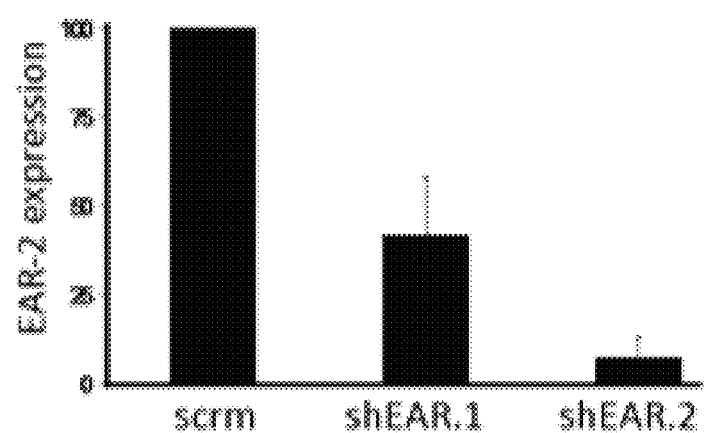
FIG. 4 shows quantification of NR2F6 (EAR-2) protein levels, determined by immunoblot and quantified using densitometry, in human U937 leukemia cells that were treated with NR2F6 shRNA or a hairpin control.
Figure 5:
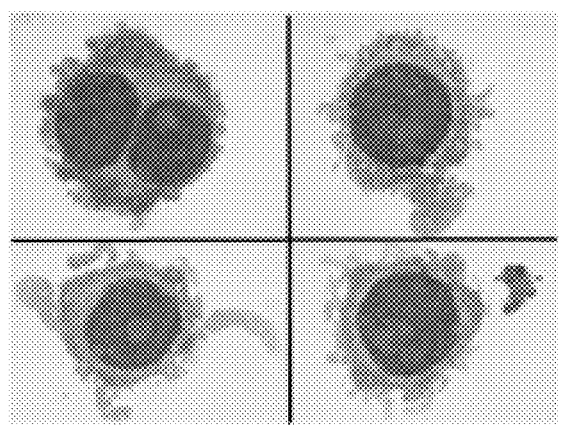
FIG. 5 shows cytospins that demonstrate morphologically that knock down of NR2F6 using short-hairpin RNAs induces terminal differentiation and blood cell maturation of U937 human leukemia cells.
Figure 5:
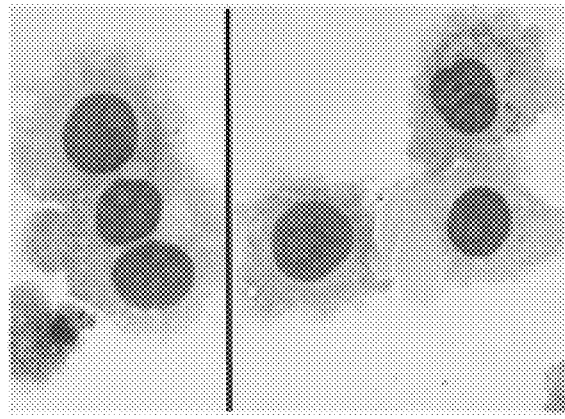
Figure 6:
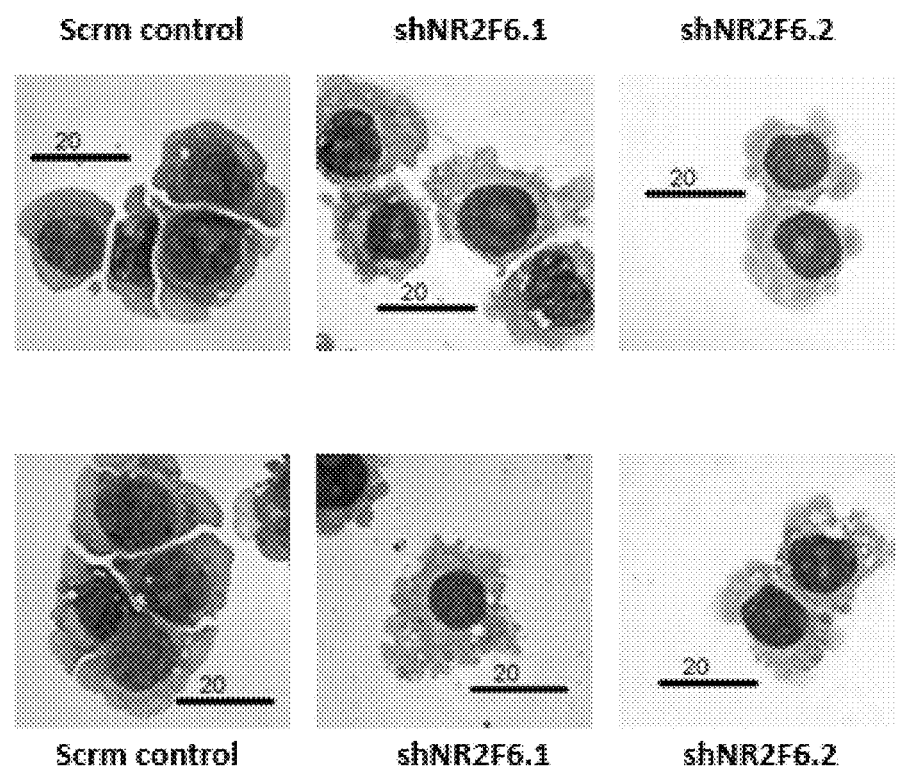
FIG. 6 shows cytospins from a second experiment that demonstrate morphologically that knock down of NR2F6 using short-hairpin RNAs induces terminal differentiation and blood cell maturation of U937 human leukemia cells.
Figure 7:
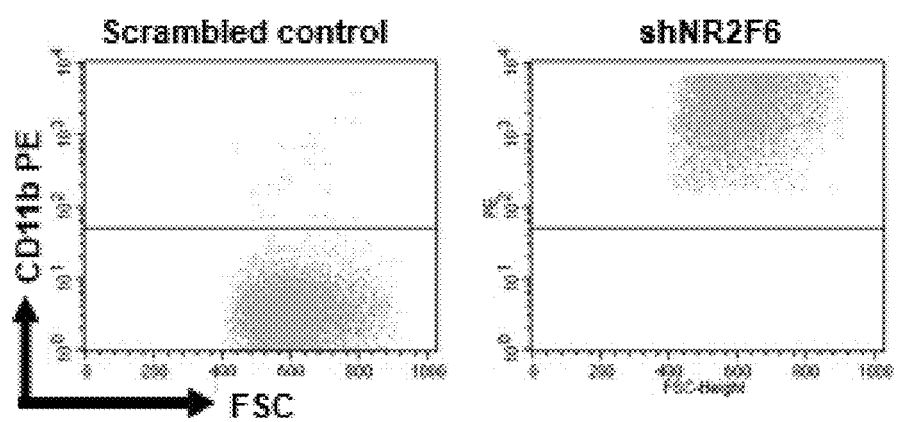
FIG. 7 shows dot plots generated by flow cytometry showing that knock down of NR2F6 using short-hairpin RNAs induces terminal differentiation and blood cell maturation of U937 human leukemia cells. These data demonstrate that knockdown of NR2F6 was sufficient to allow the leukemia cells to become mature granulocytes blood cells.
Figure 8:
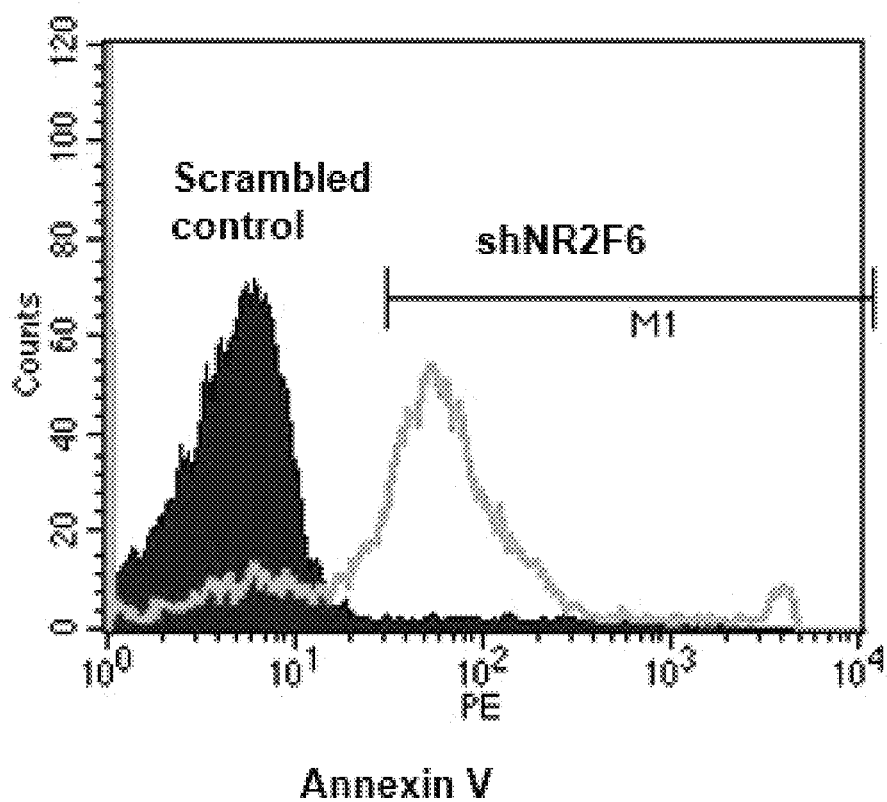
FIG. 8 shows histograms of annexin V staining generated by flow cytometry showing that knock down of NR2F6 using short-hairpin RNAs induces terminal differentiation and blood cell maturation of U937 human leukemia cells that is followed spontaneously by apoptosis (programmed cell death).

Embodiments of the present invention are described below. It is, however, expressly noted that the present invention is not limited to these embodiments, but rather the intention is that modifications that are apparent to the person skilled in the art and equivalents thereof are also included.

The term "NR2F6" as used herein refers to nuclear receptor subfamily2, group F, member 6 and is also referred to as v-erbA-related gene or ear-2 and includes, without limitation, the protein encoded by the gene having the sequence as shown in SEQ ID NO: 1 (human) or SEQ ID NO: 2 (mouse) or variants thereof and the protein having the amino acid sequence as shown in SEQ ID NO: 3 (human) or SEQ ID NO: 4 (mouse) or variants thereof.

The term "a cell" as used herein includes a plurality of cells and refers to all types of cells including hematopoietic and cancer cells. Administering a compound to a cell includes in vivo, ex vivo and in vitro treatment.

The term "stem cell" as used herein refers to a cell that has the ability for self-renewal. Non-cancerous stem cells have the ability to differentiate where they can give rise to specialized cells.

The term "effective amount" as used herein means a quantity sufficient to, when administered to an animal, effect beneficial or desired results, including clinical results, and as such, an "effective amount" depends upon the context in which it is being applied. For example, in the context of inhibiting self-renewal of stem cells, it is the amount of the NR2F6 inhibitor sufficient to achieve such an inhibition as compared to the response obtained without administration of the NR2F6 inhibitor.

The term "oligonucleotide" is intended to include unmodified DNA or RNA or modified DNA or RNA. For example, the nucleic acid molecules or polynucleotides of the disclosure can be composed of single- and double stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "animal" as used herein includes all members of the animal kingdom, preferably mammal. The term "mammal" as used herein is meant to encompass, without limitation, humans, domestic animals such as dogs, cats, horses, cattle, swine, sheep, goats, and the like, as well as wild animals. In an embodiment, the mammal is human.

The term "interfering RNA" or "RNAi" or "interfering RNA sequence" refers to double-stranded RNA (i.e., duplex RNA) that targets (i.e., silences, reduces, or inhibits) expression of a target gene (i.e., by mediating the degradation of mRNAs which are complementary to the sequence of the interfering RNA) when the interfering RNA is in the same cell as the target gene. Interfering RNA thus refers to the double stranded RNA formed by two complementary strands or by a single, self-complementary strand. Interfering RNA typically has substantial or complete identity to the target gene. The sequence of the interfering RNA can correspond to the full length target gene, or a subsequence thereof. Interfering RNA includes small-interfering RNA" or "siRNA," i.e., interfering RNA of about 15-60, 15-50, 15-50, or 15-40 (duplex) nucleotides in length, more typically about, 15-30, 15-25 or 19-25 (duplex) nucleotides in length, and is preferably about 20-24 or about 21-22 or 21-23 (duplex) nucleotides in length (e.g., each complementary sequence of the double stranded siRNA is 15-60, 15-50, 15-50, 15-40, 15-30, 15-25 or 19-25 nucleotides in length, preferably about 20-24 or about 21-22 or 21-23 nucleotides in length, and the double stranded siRNA is about 15-60, 15-50, 15-50, 15-40, 15-30, 15-25 or 19-25 preferably about 20-24 or about 21-22 or 21-23 base pairs in length). siRNA duplexes may comprise 3' overhangs of about 1 to about 4 nucleotides, preferably of about 2 to about 3 nucleotides and 5' phosphate termini. The siRNA can be chemically synthesized or maybe encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., PNAS USA 99: 9942-7 (2002); Calegari et al., PNAS USA 99: 14236 (2002); Byrom et al., Ambion Tech-Notes 10(1): 4-6 (2003); Kawasaki et al., Nucleic Acids Res. 31: 981-7 (2003); Knight and Bass, Science 293: 2269-71 (2001); and Robertson et al., J. Biol. Chem. 243: 82 (1968)). Preferably, dsRNA are at least 50 nucleotides in length, about 100, 200, 300, 400 or 500 nucleotides in length. A dsRNA may be as long as 1000, 1500, 2000, 5000 nucleotides in length, or longer. The dsRNA can encode for an entire gene transcript or a partial gene transcript.

The term "siRNA" refers to a short inhibitory RNA that can be used to silence gene expression of a specific gene. The siRNA can be a short RNA hairpin (e.g. shRNA) that activates a cellular degradation pathway directed at mRNAs corresponding to the siRNA. Methods of designing specific siRNA molecules or shRNA molecules and administering them are known to a person skilled in the art. It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can also be added.

The term "antisense nucleic acid" as used herein means a nucleotide sequence that is complementary to its target e.g. a NR2F6 transcription product. The nucleic acid can comprise DNA, RNA or a chemical analog, that binds to the messenger RNA produced by the target gene. Binding of the antisense nucleic acid prevents translation and thereby inhibits or reduces target protein expression. Antisense nucleic acid molecules may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

As used in this context, to "treat" means to ameliorate at least one symptom of the disorder. In some embodiments, a treatment can result in a reduction in tumor size or number, or a reduction in tumor growth or growth rate.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoptastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, e.g., affecting the nervous system, lung, breast, thyroid, lymphoid, gastrointestinal, and genito-urinary tract, as well as adenocarcinomas, which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The invention provides methods for treating a cellular proliferative disorder, such as neoplasia, in a mammalian subject (eg. rodent such as mouse, or primate such as human, chimpanzee or monkey). The methods include selecting a subject who is in need of treatment for a cellular proliferative disorder or a disorder of cellular differentiation, administering to the subject a therapeutically effective amount of an oligonucleotide that activates the RNA inference pathway against the gene target NR2F6, thereby treating the cellular proliferative disorder or the disorder of cellular differentiation in the subject. Disorders of cellular proliferation and differentiation is selected from the group consisting of neoplasia (cancer), hyperplasias, restenosis, cardiac hypertrophy, immune disorders and inflammation. Preferably, said cell proliferative disorder is a neoplastic disorder, i.e., cancer. In some embodiments, the cancer includes, but is not limited to papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, hepatocellular carcinoma, leukemia, lymphoma, Hodgkin's disease, osteosarcoma, testicular cancer, and Burkitt's disease. In one embodiment of the invention the oligonuclotides are used to induce a reduction of proliferation of the cancer cells. In another embodiment of the invention the oligonucleotides are used to induce the differentiation of the cancer cells. In yet another embodiment of the invention the oligonucleotides are used to specifically target the functions of the cancer stem cells.

One embodiment of the invention is a short-interfering ribonucleic acid (siRNA) molecule effective at silencing NR2F6 expression or substantially inhibiting NR2F6 expression. In one embodiment of the invention the oligonucleotide backbone is chemically modified to increase the deliverability of the interfering ribonucleic acid molecule. In another embodiment these chemical modifications act to neutralize the negative charge of the interfering ribonucleic acid molecule. One embodiment of the invention consists of a pharmaceutical composition comprising an siRNA oligonucleotide that induces RNA interference against NR2F6. It is known to one of skill in the art that siRNAs induce a sequence-specific reduction in expression of a gene by the process of RNAi, as previously mentioned. Thus, siRNA is the intermediate effector molecule of the RNAi process that is normally induced by double stranded viral infections, with the longer double stranded RNA being cleaved by naturally occurring enzymes such as DICER. Some nucleic acid molecules or constructs provided herein include double stranded RNA molecules comprising 16-30, e.g., 16, 17, 18, 19, 20, 21, 22, 23, 24, 25, 26, 27, 28, 29, or 30 nucleotides in each strand, wherein one of the strands is substantially identical, for example at least 85% (or more, as for example, 90%, 95%, or 100%) identical, e.g., having 3, 2, 1, or 0 mismatched nucleotide(s), to a target region in the mRNA of NR2F6 and the other strand is identical or substantially identical to the first strand. However, it will be appreciated that the dsRNA molecules may have any number of nucleotides in each strand which allows them to reduce the level of NR2F6 protein, or the level of a nucleic acid encoding NR2F6. The dsRNA molecules provided herein can be chemically synthesized, or can be transcribed in vitro from a DNA template, or in vivo from, e.g., shRNA, which is mentioned below. The dsRNA molecules can be designed using any method known in the art.

In one embodiment, nucleic acids provided herein can include both unmodified siRNAs and modified siRNAs as known in the art. For example, in some embodiments, siRNA derivatives can include siRNA having two complementary strands of nucleic acid, such that the two strands are crosslinked. For a specific example, a 3' OH terminus of one of the strands can be modified, or the two strands can be crosslinked and modified at the 3' OH terminus. The siRNA derivative can contain a single crosslink (one example of a useful crosslink is a psoralen crosslink). In some embodiments, the siRNA derivative has at its 3' terminus a biotin molecule (for example, a photocleavable molecule such as biotin), a peptide (as an example an HIV Tat peptide), a nanoparticle, a peptidomimetic, organic compounds, or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acids described within the practice of the current invention can include nucleic acids that are unconjugated or can be conjugated to another moiety, such as a nanoparticle, to enhance a desired property of the pharmaceutical composition. Properties useful in the development of a therapeutic agent include: a) absorption; b) efficacy; c) bioavailability; and d) half life in blood or in vivo. RNAi is believed to progress via at least one single stranded RNA intermediate, the skilled artisan will appreciate that single stranded-siRNAs (e.g., the antisense strand of a ds-siRNA) can also be designed as described herein and utilized according to the claimed methodologies.

In one embodiment the pharmaceutical composition comprises a nucleic acid-lipid particle that contains an siRNA oligonucleotide that induces RNA interference against NR2F6. In some aspects the lipid portion of the particle comprises a cationic lipid and a non-cationic lipid. In some aspects the nucleic acid-lipid particle further comprises a conjugated lipid that prevents aggregation of the particles and/or a sterol (e.g., cholesterol).

For practice of the invention, methods for expressing siRNA duplexes within cells from recombinant DNA constructs to allow longer-term target gene suppression in cells are known in the art, including mammalian Pol III promoter systems (e.g., H1 or U6/snRNA promoter systems) capable of expressing functional double-stranded siRNAs. Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression. Constructs containing siRNA sequence(s) under the control of a T7 promoter also make functional siRNAs when co-transfected into the cells with a vector expressing T7 RNA polymerase. A single construct may contain multiple sequences coding for siRNAs, such as multiple regions of the NR2F6 gene, such as a nucleic acid encoding the NR2F6 mRNA, and can be driven, for example, by separate Pol III promoter sites. In some situations it will be preferable to induce expression of the hairpin siRNA or shRNAs in a tissue specific manner in order to activate the shRNA transcription that would subsequently silence NR2F6 expression. Tissue specificity may be obtained by the use of regulatory sequences of DNA that are activated only in the desired tissue. Regulatory sequences include promoters, enhancers and other expression control elements such as polyadenylation signals. Regulatory sequences include those which direct constitutive expression of a nucleotide sequence in many types of host cell and those which direct expression of the nucleotide sequence only in certain host cells. Tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters as follows may be used to target gene expression in other tissues. Examples of more tissue specific promoters include in (a) to target the pancreas promoters for the following may be used: insulin, elastin, amylase, pdr-I, pdx-I, glucokinase; (b) to target the liver promoters for the following may be used: albumin PEPCK, HBV enhancer, a fetoprotein, apolipoprotein C, .alpha.-I antitrypsin, vitellogenin, NF-AB, Transthyretin; (c) to target the skeletal muscle promoters for the following may be used: myosin H chain, muscle creatine kinase, dystrophin, calpain p94, skeletal .alpha.-actin, fast troponin 1; (d) to target the skin promoters for the following may be used: keratin K6, keratin KI; (e) lung: CFTR, human cytokeratin IS (K 18), pulmonary surfactant proteins A, B and C, CC-10, Pi; (0 smooth muscle: sm22 .alpha., SM-.alpha.-actin; (g) to target the endothelium promoters for the following may be used: endothelin-I, E-selectin, von Willebrand factor, TIE, KDR/flk-I; (h) to target melanocytes the tyrosinase promoter may be used; (i) to target the mammary gland promoters for the following may be used: MMTV, and whey acidic protein (WAP).

Yet another embodiment of the invention consists of a pharmaceutical composition comprising an oligonucleotide that induces RNA interference against NR2F6 combined with a delivery agent such as a liposome. For more targeted delivery immunoliposomes, or liposomes containing an agent inducing selective binding to neoplastic cells may be used.

The present invention further provides pharmaceutical compositions comprising the nucleic acid-lipid particles described herein and a pharmaceutically acceptable carrier.

Another embodiment of the invention consists of a pharmaceutical composition comprising an oligonucleotide that induces RNA interference against NR2F6 combined with an additional chemotherapeutic agent.

Yet another embodiment of the invention consists of a pharmaceutical composition comprising an oligonucleotide that induces RNA interference against NR2F6 combined with an additional agent used to induce differentiation One embodiment of the invention is a short-interfering ribonucleic acid (siRNA) molecule effective at silencing NR2F6 expression that has been cloned in to an appropriate expression vector giving rise to an shRNA vector.

In certain embodiment shRNA olignucleotides are cloned in to an appropriate mammalian expression vectors, examples of appropriate vectors include but are not limited to lentiviral, retroviral or adenoviral vector.

In this embodiment, the invention consists of a viral vector, comprising the inhibitory RNA molecule described above. The viral vector preferably is a lentivirus. In one aspect the viral vector is capable of infecting cancer cells. Another embodiment is a lentivirus vector that is an integrating vector. The viral vector preferably is capable of transducing cancer cells. The viral vector is preferably packaged in a coat protein the specifically binds to cancer cells. The viral vector preferably is capable of expressing an RNA that inhibits NR2F6 expression. Another embodiment of the invention is one in which the viral vector is preferably produced by a vector transfer cassette and a separate helper plasmid. In certain embodiment the shRNA olignucleotides is combined with a pharmaceutically acceptable vehicle a pharmaceutical composition. One embodiment is a pharmaceutical composition comprising an inhibitory oligonucleotide that is a double stranded RNA molecule.

One aspect of the invention is a microRNA or family of microRNAs are administered that substantially inhibit expression of NR2F6

In one embodiment, the inhibition of NR2F6 is utilized to enhance efficacy of existing anticancer approaches, or therapies. Specifically, inhibition of NR2F6 may be combined with agents selected from a group comprising of: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

The present inventors have found that NR2F6 is a regulator of cancer cell proliferation, self-renewal and differentiation, and that silencing of NR2F6 with oligonucleotides that induce RNA interference induces a reduction of cancer cell proliferation, inhibiting clonogenicity and self-renewal of proliferating cancer cells, and induces differentiation.

Accordingly, the present disclosure provides a method of modulating cancer cell growth, proliferation and/or differentiation comprising administering an effective amount of a synthetic oligonucleotide that induces RNA interference of NR2F6 to a cell or animal in need thereof.

In one aspect, the synthetic oligonucleotide is an siRNA targetting NR2F6. In another aspect, the synthetic oligonucleotide is an shRNA targeting NR2F6. And yet in another aspect the synthetic oligonucleotide is an antisense RNA molecule targeting NR2F6.

Accordingly, the present disclosure provides a method of inhibiting self-renewal of stem cells comprising administering an effective amount of an oligonucleotides that induce RNA interference to a cell or animal in need thereof. The present disclosure also provides the use of a oligonucleotides that induce RNA interference for inhibiting self-renewal of stem cells in a cell or animal in need thereof. The present disclosure further provides the use of an oligonucleotide that induce RNA interference in the preparation of a medicament for inhibiting self-renewal of stem cells in a cell or animal in need thereof. The present disclosure also provides a oligonucleotides that induce RNA interference for use in inhibiting self-renewal of stem cells in a cell or animal in need thereof.

In another embodiment, the present disclosure provides a method of inducing terminal differentiation of stem cells comprising administering of an effective amount of oligonucleotides that induce RNA interference to NR2F6 to a cell or animal in need thereof. The present disclosure also provides the use of oligonucleotides that induce RNA interference to NR2F6 for inducing terminal differentiation of stem cells in a cell or animal in need thereof. The present disclosure further provides the use of oligonucleotides that induce RNA interference to NR2F6 in the preparation of a medicament for inducing terminal differentiation of stem cells in a cell or animal in need thereof. The present disclosure also provides oligonucleotides that induce RNA interference to NR2F6 for use in inducing terminal differentiation of stem cells in a cell or animal in need thereof.

In one embodiment, the stem cells are cancer stem cells, leukemia stem cells or ovarian cancer stem cells.

The term "inhibiting self renewal of stem cells" as used herein includes but is not limited to preventing or decreasing the clonal longevity, clonogenicity, serial replating ability, clonogenic growth and/or transplantability of the stem cells.

df The invention presents a method of identifying agonists and antagonists to the orphan nuclear receptor NR2F6 by measuring a test compound's ability to bind to a specific site on a recombinant protein (that contains the sites from the nuclear receptor NR2F6 that we show regulates its function), relative to the ability of a control known ligand whose binding abilities are known and standardized. By comparing the ability of the test compound to occupy the active site in the recombinant protein that is occupied by the known ligand, one is able to measure the binding abilities of the test compound and determine if binding occurs by measuring the occupancy of the known ligand in the active site in the presence of test compounds.

Essentially, the invention describes an NR2F6 ligand binding assay that is based on the principle of reporter displacement. This assay is based on a known ligand that acts as a reporter probe that is distinctively designed to bind to the active site (the site of interest) of NR2F6. The proximity between known ligand that acts as a reporter and the recombinant NR2F6 protein results in the emission of a signal: this signal can be measured fluorescently, radioactively, or optically using indirect methods. The basis of this assay is that test compounds that bind to the same binding site as the known ligand are displacing the probe (enzymatically-, fluorescently-, radioactively- or un-tagged known ligand) and causing signal loss. This signal is measured using standard methods, which then allows one to deduce if the test compound is binding to the NR2F6 protein, and also with what affinity binding occurs with.

The affinity and selectivity of an unlabeled ligand to compete for the binding of a fixed concentration of a radiolabeled ligand to a receptor are determined using an NR2F6 ligand binding assay as described herein.

Scintillation proximity assay relates to any method where a radioactive label is in close vicinity to matter, which is capable of transforming radioactive emission to light or other form of detectable signal. The matter can be a particle or solid-support. (Hart H. E. et al. Mol. Immunol. 1979:16; 265, Bosworth N et al. Nature 1989:341; 167)

Fluorescent ligand binding assays relates to any method where fluorescence is used to generate a detectable signal. Fluorescence has wide spectrum of wavelengths, therefore multiple colors can be applied for detection of a specific target. Currently, there are many techniques used to measure fluorescence intensity, such as fluorescence anisotropy, fluorescence correlation spectroscopy, time-resolved fluorescence, fluorescence polarization, fluorescence and bioluminescence resonance energy transfer. All these techniques are effectively used as NR2F6 ligand binding assays. Fluorescence anisotropy can be applied to measure unequal intensities of the light emitted from a fluorophore along different axes of polarization. Fluorescence correlation spectroscopy analyzes fluctuations of the fluorescence intensity, measuring the average number of fluorescent particles and diffusion time, detecting the passage of the particles through the space. Time resolved fluorescence applies convolution integral to measure the lifetime from fluorescence decay after excitation. Fluorescence polarization method detects the difference between polarization of the polarized light used to excite the fluorophore and light emitted from a fluorophore.

Importantly, resonance energy transfer methods apply labels which are attached to reactive amino acid side chains. These labels include fluorescent proteins and light-emitting enzymes. Fluorescence and bioluminescence resonance energy transfer (FRET and BRET) methods are used to monitor the distances between two labels. These methods analyze conformational changes of single protein molecules or protein-protein interactions. Furthermore, FRET method detects the non-radiative transfer of energy from one donor chromophore to an acceptor chromophore.

Fluorescence polarization assay refers to a method where polarization property of a dyed molecule is altered upon contact with another molecule. When the small dyed molecule is freely moving and rotating in medium, a low polarization value is measured because movement and rotation occurs fast. When the small dyed molecule is attached to a larger molecule such as to a particle or a protein, its polarization is altered and a larger polarization value is measured. (Park S. H. et al. Methods Mol. Biol. 2004:261; 161)

Fluorescence correlation spectroscopic assay can be constructed using a particle and a dyed substance. When the dyed substance is being attached to the particle its fluorescence fluctuation pattern alters leading to a change in signal from that of a freely fluctuating dyed substance. The method does not require particles. Proteins or cells or other larger molecules or molecule complexes can also be utilized. (Krichevsky O. at al. Rep. Prog. Phys. 2002:65; 251)

Enzyme-based assay relates to an assay format where enzyme or substrate has been attached on a compound or particle or solid-support. Soluble substrates or enzymes reacts with its binding partner generating a detectable signal.

Radioactive, radioactive based, or radioligand binding assay relates to an assay format where radioactively labeled ligand is applied in this assay to detect its binding to a target. Radioactive ligands are commonly used to measure ligand binding to receptors. In this assay, you will measure binding of a radiolabeled ligand to cells or cell membranes containing a receptor of interest. Both whole cells and cell membranes can be used for this assay. Radioligands can be used to perform saturation curves, competition and kinetic experiments. In particular, NR2F6 radioligand binding assays can determine type, anatomical distribution and density of the receptors and ligand affinity and binding sites. There are three experimental types of NR2F6 radioligand binding assays: saturation assay, competitive assay and kinetic assay. Saturation assay analyzes equilibrium binding of different concentrations of the radioactively labeled ligand to the receptor. This assay measures the tissue/cell-specific affinity and density of the analyzed receptor. In contrast, competitive assay investigates equilibrium binding of a single concentration of radioligand at different concentrations of an unlabeled competitor. Analysis of the binding data identifies the affinity of the receptor for the competitor molecule. Kinetic assay can be used to measure the time course of ligand dissociation and association.

NR2F6 radioligand binding assays can be of the filtration format, SPA format, ScreenReady™ type of assay, FlashPlate ligand binding assays, or other suitable formats.

In filtration format, the binding assay is carried out first in one assay plate, then filtered through a filtermat or UniFilter® plate using a cell harvester (vacuum manifold). The filters are washed to remove any unbound radioligand. The filtermat or UniFilter plate is then dried and scintillation cocktail (or Meltilex®) is added before reading in an appropriate detector.

In the SPA NR2F6 ligand binding format, cell membranes are captured onto SPA beads. When radioligand binds to the receptor/membrane, this puts the radiochemical into proximity of the SPA bead. The beta energy from the radioligand can interact with scintillant in the bead, producing a signal that can be measured. Radioligand that is not bound to the cell membrane will not be close enough to the SPA bead to interact strongly with the scintillant.

In the FlashPlate NR2F6 ligand binding assay format the binding characteristics of FlashPlates are similar to other polystyrene microplates, allowing the use of standard published plate-coating methods. A target receptor or receptor membrane is coated or bound onto the wall of a FlashPlate well, after which radioligands, standards, and compounds are added. Energy emitted from the radioligand can interact with scintillant embedded in the walls of the FlashPlate, producing a detectable signal. Unbound radioligand is not close enough to the walls of the plate to activate the scintillant, which allows you to distinguish radioligand bound to the receptor/membrane from radioligand free in solution. No separation step is required.

Surface plasmon resonance (SPR) relates to an assay format where the surface plasmon polaritons (SPP) which are electromagnetic waves generated when light interacts with surface charges in gold surface. The main application of SPR is to analyze the binding of the ligands to the receptors linked to a gold surface. Therefore, SPR is used to study binding kinetics. The analyzed interactions between a drug and its target include formation of a ligand-receptor complex and dissociation of this complex followed by the ligand removal. SPR is applied to follow the association and dissociation mechanisms in real time by creating a sensorgram which detects the changes in wavelength. Importantly, SPR is a quantitative method, since these changes are related to the number of bound ligand molecules. However, sensitivity of SPR is low in detection of binding-induced conformational change. SPR assay can be used for different soluble proteins including kinases and proteases.

Plasmon-waveguide resonance relates to an assay format where similarly to SPR, plasmon-waveguide resonance method also applies surface-excited plasmon. PWR uses a polarized continuous wave laser exciting electromagnetic waves in a resonator made of a thin silver film with a layer of $SiO_2$ and a glass prism. In this assay, receptors are immobilized on the outer $SiO_2$ surface. Ligand binding changes amplitude, position and width of reflected lights. In contrast to SPR, PWR examines anisotropic optical contents of receptor—ligand complexes and differentiates mass density changes from conformational changes. Thus, PWR can be applied to analyze the changes in receptor conformation and local mass density. This assay shows that distinct ligands including full agonists, partial agonists and antagonists cause distinct conformational changes in receptors. PWR has been reported to be useful tool to investigate receptor-mediated processes in real biological membranes, since it has been used to study ligand binding to membrane integral proteins obtained from bacterial and mammalian cell membranes.

SPR imaging for affinity-based biosensors relates to an assay format where an affinity-based biosensors measures the binding kinetics and is related to intensity modulation and analyzes the reflectivity of monochromatic incident p-polarized light detected at a fixed angle. This method studies binding events across the entire sensor surface. Besides, SPR imaging studies are often combined with microarrays to measure specific microspots. SPR imaging analyzes different chemical compounds for a target of interest. In addition, this method has been used for biomarker identification, for detecting microRNA and for analysis of interactions of proteins, DNA and RNA and whole cells.

Whispering gallery microresonator (WGM) relates to an assay format that is based on wave sensing and applies different microresonators or resonant cavities having high quality factors to limit light, which generates very sharp resonances for the light. Binding of molecules to the surface of the cavity induces changes of the resonant wavelength changes. The resonant changes of light permit multiple analyses of molecules. In contrast to other label-free ligand binding assays, backscattering interferometry (BSI) has an advantage as a homogenous solution-based biosensing. In particular, BSI performs determination of both on and off rate constants of binding relations. BSI has been used to detect the equilibrium dissociation constants for different types of receptor-ligand binding, including antigen-antibody interactions.

Resonant waveguide grating (RWG) relates to an assay format where an electromagnetic wave bound to the surface to analyze biomolecular interactions. In this method, light is coupled into the thin film by diffraction leading to the generation of an evanescent wave. RWG uses the surface-linked electromagnetic wave to analyze interactions between ligand and receptor. In RWG method the maximum incoupling efficiency is obtained at the resonance angle or wavelength which is a function of the local refractive index at the sensor surface. In addition, RWG is usually performed in microplate formats and is designed for affinity screening.

Biolayer Interferometry biosensor (BIB) relates to an assay format where a spectrometer is used to detect interference patterns formed by light reflected from an optical layer and a biolayer containing proteins of interest. These two types of light interact with each other and create a specific interference pattern. When ligands bind to the receptors, the inference pattern is altered. These changes of the interference pattern represented by specific peaks and troughs can be detected by a spectrometer. This method helps to study binding kinetics. Moreover, a subtype of BIB, biolayer interferometry, can be effectively used to measure ligand binding.

Agonists and antagonists may be identified using assays to detect compounds which inhibit binding of a known ligand to a recombinant protein encoding for NR2F6 in whole or in part, in either cell-free or cell based assays. We have shown that one such ligand is troglitazone. However, one skilled in the art would appreciate that any molecule that is shown to bind to NR2F6 could be used as a known ligand once binding to the NR2F6 protein is validated. Other suitable ligands could include one or more of the following, family members or analogue thereof:

N-(1-phenylethyl)quinazolin-4-amine, 1-[(4-bromophenyl)methyl]-2-methylbenzimidazole, Ambcb90456311, AGN-PC-04RX4B, Pyridaben, 4-ethoxy-N-(pyridin-4-ylmethyl)benzenesulfonamide, 4-chloro-3-ethoxy-N-(pyridin-4-ylmethyl)benzenesulfonamide, ethyl 4-(cyclohexylamino)-2-(3,5-dimethylpyrazol-1-yl)pyrimidine-5-carboxylate, ethyl 4-(cyclopentylamino)-2-(3,5-dimethylpyrazol-1-yl)pyrimidine-5-carboxylate, AGN-PC-09SAX3, SMR000064686, AGN-PC-0NLTEQ, N-[2-(3,4-dimethoxyphenyl)ethyl]thieno[2,3-d]pyrimidin-4-amine, N-[2-(3,4-dimethoxyphenyl)ethyl]-6-methylthieno[2,3-d]pyrimidin-4-amine hydrochloride, ST50323391, N-Benzylquinazolin-4-amine, ST50483228, Chlormidazole, 2-methyl-1-(2-methylbenzyl)-1H-benzimidazole, MLS001122505, Ambcb81049924, AGN-PC-04RX7E, Ambcb42757923, MLS001124721, 7-benzyl-4-chloro-5,6-dimethyl-7H-pyrrolo[2,3-d]pyrimidine, T6132867, BAS 07204618, T5546966, 4-chloro-N-(4-chlorobenzyl)-1,3-dimethyl-1H-pyrazole-5-carboxamide, Verrucarin A 9,10-epoxide, MLS002702133, Ossamycin, MLS002702060, Dihydrorotenone, N-[2-[2-[2,5-dimethyl-1-(thiophen-2-ylmethyl)pyrrol-3-yl]-2-oxoethoxy]phenyl]acetamide, 2,4,6-trimethyl-N-(pyridin-4-ylmethyl)benzene sulfonamide, BAS 05598377, 4-bromo-2,5-dimethyl-N-(pyridin-4-ylmethyl)benzene sulfonamide, 5-tert-butyl-N-[(6-fluoro-4H-1,3-benzodioxin-8-yl)methyl]-2-methylpyrazole-3-carboxamide, T6090485, MLS002548992, 5,6-dimethyl-4-[4-[2-(4-methylphenoxy)ethyl]piperazin-1-yl]thieno[2,3-d]pyrimidine, MLS002473459, MLS001030349, 4-(3,4-dihydro-1H-isoquinolin-2-yl)-5H-pyrimido[5,4-b]indole, 4-(3,4-Dihydro-1H-isoquinolin-2-yl)-8-fluoro-5H-pyrimido[5,4-b]indole, 4-[4-(4-methoxyphenyl)piperazino]-5H-pyrimido[5,4-b]indole, 4-[4-(1,3-benzodioxol-5-ylmethyl)piperazin-1-yl]-7-methoxy-5H-pyrimido[5,4-b]indole, SMR000044829, 8-fluoro-N-(3-propan-2-yloxypropyl)-5H-pyrimido[5,4-b]indol-4-amine, GNF-Pf-1678, MLS003116118, 2-[4-(5-methyl-[1,2,4]triazolo[1,5-a]pyrimidin-7-yl)piperazin-1-yl]-1,3-benzothiazole, 5-methyl-3,6-diphenylpyrazolo[1,5-a]pyrimidin-7-amine, 4-[4-[(4-chlorophenyl)methyl]piperazin-1-yl]-1-[(4-methylphenyl)methyl]pyrazolo[3,4-d]pyrimidine, MLS002632722, MLS002477203, MLS003120814, AGN-PC-07AHX3, MLS003120821, MLS003120807, MLS003120811, MLS003120820, ethyl 4-[[1-(2,4-dimethylphenyl)pyrazolo[3,4-d]pyrimidin-4-yl]amino]piperidine-1-carboxylate, AGF-87638, ZINC03428816, CHEMBL493153, N-[4-(2-methyl-1-methylsulfonyl-2,3-dihydroindol-5-yl)-1,3-thiazol-2-yl]-2-thiophen-2-ylacetamide, F0558-0175, AC1MLRO7, 4-(2-methylimidazo[1,2-a]pyridin-3-yl)-N-(3-methylphenyl)-1,3-thiazol-2-amine, AGN-PC-09PPXW, Compound 15Jf, AC1MEEXM, AC1OBZ0O, ST4126227, SMR000718391, MLS002694437, MLS003119103, AGN- PC-04V4GP, MLS000562030, AGN-PC-00YPMB, T5400648, Streptovitacin, CAS-66-81-9, Cycloheximide, ACTIPHENOL, TCMDC-125620, 1-[1,1'-Biphenyl]-4-yl-2-(4-imino-1(4H)-pyridinyl)ethanone, SMR000036350, MLS000080109, MLS000080126, Ambcb40308772, MLS000733369, Ambcb20390854, MLS000732313, AGN-PC-04RYS6, Ambcb33735952, AGN-PC-04RYKA, MLS000733096, Ambcb63657849, MLS001090213, MLS003678910, AC1OXF5M, SMR000218920, MLS000037490, Boc-KS, MLS000734694, AGN-PC-087SDW, ISUPSL100073, 4-{[5,7-bis(trifluoromethyl)[1,8]naphthyridin-2-yl]oxy}benzenol, MLS001144057 MLS001250118, MLS003120011, 3-(Toluene-4-sulfonylmethyl)-2,3-dihydro-benzo[4,5]imidazo[2,1-b]thiazole, T0508-0735, Carboxyamidotriazole, MLS003116132, SMR000623161, ASN 09858385, T6069554, T6302989, SMR000629820, SMR000629835, MLS001028777, MLS001028747, MLS001028806, SMR000625125, T5403634, T5459762, T5626573, T5337170 SMR000093473, SMR000274842, T5565081, 6-chloro-N-[3-[(4-methoxyphenyl)sulfamoyl]phenyl]pyridine-3-carboxamide, N-methyl-N-[(1,3,5-trimethylpyrazol-4-yl)methyl]naphthalene-2-sulfonamide, T6099016, T6094971, ASN 04448329, SMR000241542, AGN-PC-03RL0E, AGN-PC-080KFN, T6151837, AGN-PC-0KIUAY, N-[4-(4-methylphenyl)-1,3-thiazol-2-yl]-1-thiophen-2-ylsulfonylpiperidine-4-carboxamide, 5-(3,5-dimethylpiperidin-1-yl)sulfonyl-N,N-diethyl-3-methyl-1-benzofuran-2-carboxamide, SMR000124769, N-(1-benzylpiperidin-4-yl)-1-(5-chloro-2-methylphenyl)sulfonylpiperidine-4-carboxamide, MLS001095722, MLS000735463, MLS000687652, AGN-PC-093SBW, AG-401/42008258, 5L-526S, 2-[[5-(3-chloro-1-benzothiophen-2-yl)-1,3,4-oxadiazol-2-yl]sulfanyl]acetonitrile, 2-(5-Pyridin-3-yl-[1,3,4]thiadiazol-2-ylsulfanyl)-N-quinolin-4-ylacetamide, 2-[[5-(benzotriazol-1-ylmethyl)-1,3,4-oxadiazol-2-yl]sulfanyl]-N-[(4-chlorophenyl)methyl]-N-phenylacetamide 2-[[5-(benzotriazol-1-ylmethyl)-1,3,4-oxadiazol-2-yl]sulfanyl]-N-[(4-fluorophenyl)methyl]-N-phenylacetamide, N-(2,4-difluorophenyl)-4-[5-(trifluoromethyl)pyridin-2-yl]-1,4-diazepane-1-carbothioamide, T0512-9975, [[2,7-bis(2-morpholin-4-ylethoxy)fluoren-9-ylidene]amino]thiourea, MLS001018548, T0507-0244, 4-(4-acetylphenyl)-N-(4-phenoxyphenyl)piperazine-1-carbothioamide, N-(3-ethoxypropyl)-4-[4-(4-fluorophenyl)-1,3-thiazol-2-yl]piperazine-1-carbothioamide, (+)-Emetine dihydrochloride hydrate, MLS002302684, 4-(6-chloro-1,3-benzothiazol-2-yl)-N-(2-chloro-6-methylphenyl)-1,4-diazepane-1-carboxamide, N-(3-chloro-2-methylphenyl)-4-(3-phenyl-1,2,4-thiadiazol-5-yl)-1,4-diazepane-1-carboxamide Suitable cell-free assays may be readily determined by one of skill in the art. For example, an ELISA format may be used in which purified known ligand or a purified derivative of the known ligand, such as a fusion protein is immobilized on a suitable surface, either directly or indirectly (e.g., via an antibody or to the fused epitope or protein domain) and candidate compounds are identified by their ability to block binding of purified soluble, known ligand.

The binding of unknown agonists or antagonists could be detected by using a label directly or indirectly associated with the known ligand. Suitable detection systems include the streptavidin horseradish peroxidase conjugate, or direct conjugation by a tag, e.g., fluorescein. Conversely, purified, soluble known ligand may be immobilized on a suitable surface, and candidate compounds identified by their ability to block binding of purified protein encoding in part or in whole a recombinant protein with at least 70% homology to NR2F6. The binding of unknown agonists or antagonists could be detected by using a label directly or indirectly associated with the known ligand. Many other assay formats are possible that use the NR2F6 protein and its ligands.

Suitable cell based assays may be readily determined by one of skill in the art. In general, such screening procedures involve producing appropriate cells which express the NR2F6 receptor polypeptides on the surface or interior thereof. Such cells include cells from mammals, yeast, *Drosophila* or *E. coli*. Cells expressing the receptor are then contacted with a ligand, or test compound to observe binding, or stimulation or inhibition of a functional response. The assays may simply test binding of a candidate compound wherein adherence to the cells bearing the receptor is detected by means of a label directly or indirectly associated with the candidate compound or in an assay involving competition with a labeled competitor, such as the known ligands. Alternatively, cells expressing the ligand are then contacted with a receptor, such NR2F6, or test compound to observe binding, or stimulation or inhibition of a functional response. Similarly, the assays may simply test binding of a candidate compound wherein adherence to the cells bearing the ligand is detected by means of a label directly or indirectly associated with the candidate compound or in an assay involving competition with a labeled competitor. Further, these assays may test whether the candidate compound results in a signal generated by activation of the receptor or its respective ligand using detection systems appropriate to the cells bearing the receptor or its ligand and fusion proteins thereof at their surfaces. Inhibitors of activation are generally assayed in the presence of an agonist, such as the ligand troglitazone for cells expressing NR2F6 and the effect on activation by the agonist by the presence of the candidate compound is observed. Standard methods for conducting such screening assays are well understood in the art.

Examples of potential agonists to NR2F6 include antibodies that bind to its ligand bind domain, or derivatives thereof, and small molecules that bind to its ligand binding domain, or to allosteric sites. These agonists will elicit a response mimicking all or part of the response induced by contacting the native ligand, if such a molecule exists. Alternatively, NR2F6 protein may be expressed as a soluble protein, including versions which fuse all or part of NR2F6 with a convenient partner peptide for which detection reagents are available, eg NR2F6-IgG or NR2F6-IgG fusions, and used in a solid state or solution phase binding assay. For example, the soluble NR2F6 can be used to detect agonist or antagonist binding directly through changes that can be detected experimentally, eg surface plasmon resonance, nuclear magnetic resonance spectrometry, sedimentation, calorimetry. The soluble NR2F6 can be used to detect agonist or antagonist binding indirectly by looking for competition of the candidate agonist or antagonist with a ligand, whose binding can be detected. Ligand detection methods include antibody recognition, modification of the ligand via radioactive labeling, chemical modification (eg biotinylation), fusion to an epitope tag. Methods include but are not limited to ELISA based assays, immunoprecipitation and scintillation proximity.

Assays similar to those described above using soluble or bound recombinant NR2F6 protein may also be used to identify and purify additional natural or synthetic ligand(s) of NR2F6. These ligands may be agonists or antagonists of the receptor The invention presents a method of identifying agonists and antagonists to the orphan nuclear receptor NR2F6 by measuring a test compound's ability to bind to a specific site on a recombinant protein (that contains the sites from the nuclear receptor NR2F6 that regulates its function), relative to the ability of a control known ligand whose binding abilities are known and standardized. By comparing the ability of the test compound to occupy the active site in the recombinant protein that is occupied by the known ligand, one is able to measure the binding abilities of the test compound and determine if binding occurs by measuring the occupancy of the known ligand in the active site in the presence of test compounds.

The invention presents a NR2F6 ligand binding assay, that is based on the affinity and selectivity of an unlabeled test compound to compete for the binding of a fixed concentration of a known ligand binds to the receptor.

In one embodiment the known ligand is radiolabelled. In one embodiment the text compound's ability to bind to the recombinant protein is achieved using saturation binding analysis, scatchard plots, non-linear curve fitting programs, competition binding, scintillation proximity assays, radioligand binding filtration assay.

One such assay can be the performed by immobilizing the portion of the NR2F6 recombinant protein directly to crystal lattice beads, available from Perkin Elmer, via a number of coupling methods. In the SPA format, recombinant protein containing sites critical to NR2F6 activation is captured onto SPA beads. The principle of receptor-binding scintillation proximity assays involves radiolabeled ligands, using 3H or 125I, binding to a receptor immobilized on the surface of a SPA bead. The bound ligand is held in close enough proximity to the bead to stimulate scintillant within the bead to emit light. Unbound radioligand is too distant from the bead to transfer energy and therefore goes undetected.

One embodiment is to detected ligand binding of test compounds using the SPA method, using a pre-coupled format.

In another embodiment one detects ligand binding of test compounds using the SPA method, Simultaneous addition ("T=0") format.

In another embodiment one detects ligand binding of test compounds using the SPA method using the delayed addition format One embodiment is to detected ligand binding of test compounds using the radioligand binding filtration assay In another embodiment the known ligand is fluorescently labeled. In one embodiment the text compound's ability to bind to the recombinant protein is achieved using Fluorescence polarization (FP) or variants thereof.

In one embodiment the text compound's ability to bind to the recombinant protein is achieved using Fluorescence resonance energy transfer (FRET) or variants thereof.

In another embodiment the known ligand is unlabeled and detection of the displacement of the known ligand is measured indirectly. In one embodiment, detection of the binding of the test compound/known ligand is done using the method of Surface Plasmon Resonance (SPR).

In one embodiment the test compound is analyzed using a competition binding assay.

Another aspect of the invention is a nuclear receptor-peptide assay for identifying ligands. This assay utilizes fluorescence resonance energy transfer (FRET) and can be used to test whether putative ligands bind to NR2F6. In FRET, a fluorescent donor molecule transfers energy via a non-radiative dipole-dipole interaction to an acceptor molecule (which is usually a fluorescent molecule). FRET is a standard spectroscopic technique for measuring distances in the 10-70A range. Upon energy transfer, which depends on the $R''^6$ distance between the donor and acceptor, the donor's fluorescence is reduced, and the acceptor fluorescence is increased, or sensitized. FRET is frequently used in both polymer science and structural biology and has recently been used to study macromolecular complexes of DNA, RNA, and proteins. In addition, Mathis has used europium cryptates with the multichromophoric Allophycocanin to achieve an extremely large $R_0$ of 90A.

In one embodiment the assay is a label-free NR2F6 ligand binding assays. One variant of the label-free ligand binding assay is surface plasmon resonance (SPR). SPR applies light-excited surface plasmon polaritons to track the binding of ligands to the receptors bound to a gold surface.

In another embodiment the assay is a label-free NR2F6 ligand binding assays. Another variant of the label-free ligand binding assay is the plasmon-waveguide resonance (PWR). PWR applies a polarized continuous wave laser exciting electromagnetic waves in a resonator made of a thin silver film with a layer of SiO2 and a glass prism. Ligand binding changes amplitude, position and width of reflected lights.

In another embodiment the assay is a label-free NR2F6 ligand binding assays. Another variant of the label-free ligand binding assay is the SPR imaging for affinity-based biosensors. This assay measures the binding kinetics and is related to intensity modulation and analyzes the reflectivity of monochromatic incident p-polarized light detected at a fixed angle.

In another embodiment the assay is a label-free NR2F6 ligand binding assays. Another variant of the label-free ligand binding assay is the Whispering gallery microresonator (WGM). WGM is based on wave sensoring binding of molecules to the surface of the cavity induces changes of the resonant wavelength changes. The resonant changes of light permit multiple analyses of molecules.

In another embodiment the assay is a label-free NR2F6 ligand binding assays. Another variant of the label-free ligand binding assay is the Resonant waveguide grating (RWG). RWG uses a nanograting to couple light into the waveguide via diffraction. The light illuminates the biosensors in microplate at a nominally normal incident angle. The drug binding of the immobilized receptors results in a shift in the resonant wavelength.

In another embodiment the assay is a label-free NR2F6 ligand binding assays. Another variant of the label-free ligand binding assay is the Biolayer Interferometry Biosensor (BIB). This assay uses a spectrometer to detect interference patterns formed by light reflected from an optical layer and a biolayer containing proteins of interest.

In one embodiment the NR2F6 ligand binding assay is a Scintillation Proximity Assay (SPA).

The scintillation proximity assay format has the advantage that it is a single step assay format. In this assay there is no need to separate bound isotope from free. The reason that one can run a homogeneous assay format is because of the development of beads impregnated with scintillant. Once the receptor is attached to the bead, and ligand is bound, they are sufficiently close to allow the β-emission from the tritium to be absorbed by the scintillant which will then shift this energy to produce light. β emissions from unbound tritiated ligand will dissipate in the buffer.

The following are components of the Scintillation Proximity Assay (SPA) type of assay system, although other variants of the SPA format may be conceived:

Solubilized receptors, or cell membrane expressing receptor of interest

Radiolabeled known ligand

Unlabeled ligand as control for non-specific binding
Ligands and test compounds as appropriate
SPA beads (See Products and catalog numbers section below)
Microplates (Refer to table in next section for catalog numbers)
Adhesive plate seal.
Appropriate detection instrument (We recommend a TopCount® or MicroBeta® Microplate Scintillation Counter for SPA scintillation beads, or a ViewLux™ CCD Imager for SPA imaging beads.)

When using a SPA recombinant NR2F6 maybe prepared from a number of different sources including: Solubilized receptors from tissues and cultured cells, whole cells, soluble purified receptors, cell membrane preparations from tissue, cell membrane preparations from cultured cells However, the preferred embodiment is soluble purified receptors.

There are a number of critical steps for using the scintillation proximity assay method of measuring test compounds. Selection of a suitable known ligand is important. The preferred embodiment is use of troglitazone, however the following chemicals or their family members may also be suitable N-(1-phenylethyl)quinazolin-4-amine, 1-[(4-bromophenyl)methyl]-2-methylbenzimidazole, Ambcb90456311, AGN-PC-04RX4B, Pyridaben, 4-ethoxy-N-(pyridin-4-ylmethyl)benzenesulfonamide, 4-chloro-3-ethoxy-N-(pyridin-4-ylmethyl)benzenesulfonamide, ethyl 4-(cyclohexylamino)-2-(3,5-dimethylpyrazol-1-yl)pyrimidine-5-carboxylate, ethyl 4-(cyclopentylamino)-2-(3,5-dimethylpyrazol-1-yl)pyrimidine-5-carboxylate, AGN-PC-09SAX3, SMR000064686, AGN-PC-0NLTEQ, N-[2-(3,4-dimethoxyphenyl)ethyl]thieno[2,3-d]pyrimidin-4-amine, N-[2-(3,4-dimethoxyphenyl)ethyl]-6-methylthieno[2,3-d]pyrimidin-4-amine hydrochloride, ST50323391, N-Benzylquinazolin-4-amine, ST50483228, Chlormidazole, 2-methyl-1-(2-methylbenzyl)-1H-benzimidazole, MLS001122505, Ambcb81049924, AGN-PC-04RX7E, Ambcb42757923, MLS001124721, 7-benzyl-4-chloro-5,6-dimethyl-7H-pyrrolo[2,3-d]pyrimidine, T6132867, BAS 07204618, T5546966, 4-chloro-N-(4-chlorobenzyl)-1,3-dimethyl-1H-pyrazole-5-carboxamide, Verrucarin A 9,10-epoxide, MLS002702133, Ossamycin, MLS002702060, Dihydrorotenone, N-[2-[2-[2,5-dimethyl-1-(thiophen-2-ylmethyl)pyrrol-3-yl]-2-oxoethoxy]phenyl]acetamide, 2,4,6-trimethyl-N-(pyridin-4-ylmethyl)benzene sulfonamide, BAS 05598377, 4-bromo-2,5-dimethyl-N-(pyridin-4-ylmethyl)benzene sulfonamide, 5-tert-butyl-N-[(6-fluoro-4H-1,3-benzodioxin-8-yl)methyl]-2-methylpyrazole-3-carboxamide, T6090485, MLS002548992, 5,6-dimethyl-4-[4-[2-(4-methylphenoxy)ethyl]piperazin-1-yl]thieno[2,3-d]pyrimidine, MLS002473459, MLS001030349, 4-(3,4-dihydro-1H-isoquinolin-2-yl)-5H-pyrimido[5,4-b]indole, 4-(3,4-Dihydro-1H-isoquinolin-2-yl)-8-fluoro-5H-pyrimido[5,4-b]indole, 4-[4-(4-methoxyphenyl)piperazino]-5H-pyrimido[5,4-b]indole, 4-[4-(1,3-benzodioxol-5-ylmethyl)piperazin-1-yl]-7-methoxy-5H-pyrimido[5,4-b]indole, SMR000044829, 8-fluoro-N-(3-propan-2-yloxypropyl)-5H-pyrimido[5,4-b]indol-4-amine, GNF-Pf-1678, MLS003116118, 2-[4-(5-methyl-[1,2,4]triazolo[1,5-a]pyrimidin-7-yl)piperazin-1-yl]-1,3-benzothiazole, 5-methyl-3,6-diphenylpyrazolo[1,5-a]pyrimidin-7-amine, 4-[4-[(4-chlorophenyl)methyl]piperazin-1-yl]-1-[(4-methylphenyl)methyl]pyrazolo[3,4-d]pyrimidine, MLS002632722, MLS002477203, MLS003120814, AGN-PC-07AHX3, MLS003120821, MLS003120807, MLS003120811, MLS003120820, ethyl 4-[[1-(2,4-dimethylphenyl)pyrazolo[3,4-d]pyrimidin-4-yl]amino]piperidine-1-carboxylate, AG-F-87638, ZINC03428816, CHEMBL493153, N-[4-(2-methyl-1-methylsulfonyl-2,3-dihydroindol-5-yl)-1,3-thiazol-2-yl]-2-thiophen-2-ylacetamide, F0558-0175, AC1MLRO7, 4-(2-methylimidazo[1,2-a]pyridin-3-yl)-N-(3-methylphenyl)-1,3-thiazol-2-amine, AGN-PC-09PPXW, Compound 15Jf, AC1MEEXM, AC1OBZ0O, ST4126227, SMR000718391, MLS002694437, MLS003119103, AGN-PC-04V4GP, MLS000562030, AGN-PC-00YPMB, T5400648, Streptovitacin, CAS-66-81-9, Cycloheximide, ACTIPHENOL, TCMDC-125620, 1-[1,1'-Biphenyl]-4-yl-2-(4-imino-1(4H)-pyridinyl)ethanone, SMR000036350, MLS000080109, MLS000080126, Ambcb40308772, MLS000733369, Ambcb20390854, MLS000732313, AGN-PC-04RYS6, Ambcb33735952, AGN-PC-04RYKA, MLS000733096, Ambcb63657849, MLS001090213, MLS003678910, AC1OXF5M, SMR000218920, MLS000037490, Boc-KS, MLS000734694, AGN-PC-087SDW, ISUPSL100073, 4-{[5,7-bis(trifluoromethyl)[1,8]naphthyridin-2-yl]oxy}benzenol, MLS001144057 MLS001250118, MLS003120011, 3-(Toluene-4-sulfonylmethyl)-2,3-dihydro-benzo[4,5]imidazo[2,1-b]thiazole, T0508-0735, Carboxyamidotriazole, MLS003116132, SMR000623161, ASN 09858385, T6069554, T6302989, SMR000629820, SMR000629835, MLS001028777, MLS001028747, MLS001028806, SMR000625125, T5403634, T5459762, T5626573, T5337170 SMR000093473, SMR000274842, T5565081, 6-chloro-N-[3-[(4-methoxyphenyl)sulfamoyl]phenyl]pyridine-3-carboxamide, N-methyl-N-[(1,3,5-trimethylpyrazol-4-yl)methyl]naphthalene-2-sulfonamide, T6099016, T6094971, ASN 04448329, SMR000241542, AGN-PC-03RL0E, AGN-PC-080KFN, T6151837, AGN-PC-0KIUAY, N-[4-(4-methylphenyl)-1,3-thiazol-2-yl]-1-thiophen-2-ylsulfonylpiperidine-4-carboxamide, 5-(3,5-dimethylpiperidin-1-yl)sulfonyl-yl)sulfonyl-N,N-diethyl-3-methyl-1-benzofuran-2-carboxamide, SMR000124769, N-(1-benzylpiperidin-4-yl)-1-(5-chloro-2-methylphenyl)sulfonylpiperidine-4-carboxamide, MLS001095722, MLS000735463, MLS000687652, AGN-PC-093SBW, AG-401/42008258, 5L -526S, 2-[[5-(3-chloro-1-benzothiophen-2-yl)-1,3,4-oxadiazol-2-yl]sulfanyl]acetonitrile, 2-(5-Pyridin-3-yl-[1,3,4]thiadiazol-2-ylsulfanyl)-N-quinolin-4-ylacetamide, 2-[[5-(benzotriazol-1-ylmethyl)-1,3,4-oxadiazol-2-yl]sulfanyl]-N-[(4-chlorophenyl)methyl]-N-phenylacetamide 2-[[5-(benzotriazol-1-ylmethyl)-1,3,4-oxadiazol-2-yl]sulfanyl]-N-[(4-fluorophenyl)methyl]-N-phenylacetamide, N-(2,4-difluorophenyl)-4-[5-(trifluoromethyl)pyridin-2-yl]-1,4-diazepane-1-carbothioamide, T0512-9975, [[2,7-bis(2-morpholin-4-ylethoxy)fluoren-9-ylidene]amino]thiourea, MLS001018548, T0507-0244, 4-(4-acetylphenyl)-N-(4-phenoxyphenyl)piperazine-1-carbothioamide, N-(3-ethoxypropyl)-4-[4-(4-fluorophenyl)-1,3-thiazol-2-yl]piperazine-1-carbothioamide, (+)-Emetine dihydrochloride hydrate, MLS002302684, 4-(6-chloro-1,3-benzothiazol-2-yl)-N-(2-chloro-6-methylphenyl)-1,4-diazepane-1-carboxamide, N-(3-chloro-2-methylphenyl)-4-(3-phenyl-1,2,4-thiadiazol-5-yl)-1,4-diazepane-1-carboxamide Cell lines may be used for receptor screening. If a cell line is selected as the source of recombinant or endogenous NR2F6, again the density of receptors is important, particularly if the ligand is of low specific activity. Typical expression levels in the region of 50,000 receptors per cell are required for 125I-ligands (~2,000 Ci mmol-1). This corresponds to approximately 200 fmols/mg membrane protein. Higher expression levels of the order of 500,000 receptors per cell are often required for 3H-ligands (20-80 Ci mmol-1), corresponding to densities greater than 2 pmoles/mg membrane protein.

The affinity of the radioligand for the receptor is another factor that should be taken into account. In practice this means that for systems where the receptor density is low, 125I-labeled ligands are usually employed. Also, if the affinity of ligand for the receptor is low (i.e. >10 nM) the signal obtained may well be quite small. For systems where the receptor density is high, either 3H- or 125I-radioligands may be used if the affinity for the receptor is also high (i.e. <10 mM); if the affinity of the ligand for the receptor is low (i.e. >10 nM), 125I is probably the radioisotope of choice for labeling. All the figures quoted are rough guides and take account of the absolute level of signal that the user requires in the assay.

Other aspects important to the enablement of the SPA type of NR2F6 ligand binding assay include the selection of assay buffer. This is usually very similar to the standard buffer and could include TRIS, HEPES, PBS, MOPS or PIPES. It should include any cofactors required for ligand binding and any essential protease inhibitors. The addition of protease inhibitors is of particular importance if using the SPA type of assay. Protease inhibitors help prevent the degradation of the receptor or the ligand during the longer equilibration periods often required. One of the most common methods to help reduce NRS is to add a nonspecific protein carrier such as BSA, peptone or casein. The effective concentration must be determined experimentally but usually will start around 0.01% (w/v) in the final assay buffer. Small amounts of various detergents may also be used to help reduce nonspecific binding. They include PEI, CHAPS, SDS, Triton X-100, Tween-20 and others, again in similar concentrations that start at 0.001%. It is important to note that the detergent used not disrupt the receptor-ligand interaction or membrane structure. Other components that can be added to the assay buffer to help reduce nonspecific binding or increase the specific signal include DTT, dimethylsulfoxide (DMSO) and various other salts such as KCl, NaCL, $MgCl_2$, and $MnCl_2$. Additionally, various cellular components may also reduce nonspecific binding. These can include RNA, DNA and proteins similar to the ligand found in the assay. In addition to nonspecific binding, the volume of the assay should be highest that it allows. This will keep the nonproximity effect to a minimum when using 125I or higher-energy isotopes.

Furthermore, one wishing to enable the SPA type of NR2F6 ligand binding assay needs to select the type of bead on to which they wish to immobilize the recombinant NR2F6 recombinant protein. Two bead types are available; they are the WGA-PVT bead (Amersham Code No. RPNQ0001) and PLYS bead (Amersham Code No. RPNQ0010). The WGA-PVT bead has been widely used for receptor assays; it is the bead of choice because the density of the bead is 1.05 g/cm3 and is therefore very amenable to automation. WGA-PVT beads bind to N-acetyl-β-D-glucosamine residues in membranes and selects for membrane glycolipids and glycoproteins. The binding capacity of WGA-PVT beads is typically 10-30μ g membrane protein per mg of bead. However, glycosylated ligands will bind nonspecifically to WGA-PVT beads. Also, some ligands may interact with the PVT core, in which case PL-YS beads may be more appropriate. In the case of PL-YS beads, there is an electrostatic interaction between negatively charged membranes and the positively charged beads. The interaction is nonselective and therefore negatively charged ligands will bind to these beads. The typical capacity of these beads is 10μ g membrane protein per mg of bead. With both bead types, it is important to confirm that there is little or no non-specific interaction of the radioligand with the bead. These controls can take the form of a no membrane control, or alternatively, the use for example of a membrane preparation from the parental cell line in the case of transfected cell lines. Sometimes it is possible to reduce non-specific interactions by the addition of various reagents e.g. BSA, detergent or by variation of the ionic strength of the buffer.

Furthermore, one wishing to enable the SPA type of ligand binding assay needs to consider the assay format. There are three possible formats for the assay that can be selected: 1) precoupled bead, 2) T0 addition and 3) delayed addition. 1) The pre-coupled bead format involves coupling the recombinant NR2F6 receptor to the beads prior to assay. In this format, a bead and the NR2F6 recombinant protein are pre-mixed to form a capture reagent. Excess receptor prep should be removed by washing to maximize binding to coupled NR2F6 receptor vs. free unbound NR2F6 receptor. The pre-coupled bead format reduces the number of additions made to the assay as the beads and membranes are added as a single reagent. One should be aware that orientation of receptor binding is not controllable, and hence not all receptor bound to the bead may be in an orientation capable of binding ligand. With this method, the receptor to bead ratio is carefully optimized and hence lower nonspecific binding and better signal to noise ratios may be obtained. Precoupling recombinant NR2F6 to beads means that one pipetting step is eliminated, an advantage for high throughput screening (HTS). Although SPA technology has been designed for HTS applications, it can also be applied to secondary screening applications such as the measurement of 'on' and 'off' rates. For these studies, the use of precoupled bead format is necessary to avoid interference of association of NR2F6 receptor and bead. 2) The T0 addition format involves the sequential addition of test samples, radio-ligand, NR2F6 receptor and bead as separate additions. The dispensing of the reagents is simple and the assay format is similar to a filtration format. The T=0 and delayed addition formats are the least complicated formats to use when optimizing the membrane and bead amounts in the assay. In general, a slight excess of bead over membrane is required to ensure complete capture of all the cell membrane present in the assay. The incubation time needed to reach equilibrium may be somewhat longer as compared to the delayed addition format. The coupling of NR2F6 to beads occurs simultaneously with ligand receptor binding. This is the most widely used format for screening assays. This format is easy to automate, but excess bead is required to capture all the NR2F6 receptor. 3) Delayed addition format. This assay format is another format which closely approximates the common filtration format or standard solution binding assay formats used for receptor binding. For the delayed addition format test samples, radioligand and NR2F6 receptor are allowed to equilibrate prior to addition of beads. SPA bead is added to the assay after the ligand has bound to the receptor, thus avoiding the bead interference with ligand binding. The incubation times for this format may also be slightly shorter than the T=0 addition format. Once the receptor ligand assay has equilibrated, the beads are added and a further 30-40 minutes are required to ensure that the bead captures the membrane. One disadvantage of this approach is that the addition of the SPA bead, after pre-equilibration of ligand and receptor preparation, causes an increase in volume and hence a reduction in the concentrations of the other assay components. This necessarily causes a shift in the assay equilibrium. The extent to which this effect is observed will depend on the rates of association and dissociation of the radiolabeled ligand to and from the receptor.

Yet another aspect of one wishing to enable the SPA type of NR2F6 ligand binding assay needs to consider the optimization of both the NR2F6 receptor bead ratio and the actual amounts of these components required to achieve the desired signal to noise ratio. The objective is to obtain a signal for further optimization.

For the precoupled bead format this involves incubating varying concentrations of NR2F6 receptor with a fixed amount of bead; aliquots are taken and B0/NSB values are measured. In the case of the T0 and delayed addition formats this optimization process involves setting up a matrix, varying the quantities of NR2F6 protein and bead; B0/NSB values are measured. In these experiments a fixed quantity of radioligand is added; this quantity will depend on the affinity of the radioligand for its receptor and should be a concentration at or around Kd. For 125I ligands, typically quantities of membrane protein between 1 and 100 µg with bead weights between 0.5 and 2.0 mg per well should be investigated. The corresponding figures for 3H ligands are 10 to 100 µg membrane protein and up to 4.0 mg of bead per well. These differences essentially reflect the relative specific activities of radioligands labeled with these isotopes.

Furthermore, one wishing to enable the SPA type of NR2F6 ligand binding assay needs to optimize ligand concentration. The volume of the assay buffer and concentration of ligand is varied to optimize the signal and can easily be performed in a matrix format. The objective of varying these parameters is:

to maximize the signal to noise ratio
to increase the signal in systems where the affinity of the ligand for the receptor is relatively low.

This can be achieved by either using increased quantities of labeled ligand and/or decreasing the assay volume, but a consequence is that the non-proximity effect component of the nonspecific binding may be increased; also sensitivity may be affected.

The determination of a counting window is another factor that should be taken into account when enabling the SPA ligand binding assay. Time course experiments should be performed to establish both the incubation time required for the attainment of equilibrium and the stability of the SPA counts at equilibrium. This should determine the 'time window' for the counting of a particular SPA receptor assay over which the equilibrated counts are stable. The period of time required for equilibrium to be established in an SPA receptor assay can often be reduced by the agitation of the assay tubes or plates on an orbital or vibrational shaker. The effect of agitation on the assay equilibrium can depend upon both the SPA bead type, the assay format and type of vial or plate employed. Agitation is desirable for assays employing WGA-PVT beads, but is essential for assays employing PL-YS beads because of the higher density of these latter beads and hence much more rapid rate of settling. Consequently, the effect of agitation on the time required to reach stable equilibrium should be investigated for each receptor studied. In T0 addition assays, the equilibrium rate is determined by the rates of association of both the membrane preparation with the SPA bead and of the labeled ligand with the membrane bound receptor. The rate of association of membranes with WGA-PVT and PL-YS beads is relatively rapid (20-60 minutes). Therefore, in many cases, the ligand binds to membranes already coupled to beads and the equilibration rate is mainly determined by the rate of association of the ligand with the receptor. Because SPA receptor assays are equilibrium assays, the stability of all assay components should be considered.

Finally, one wishing to enable the SPA NR2F6 ligand binding assay needs to perform assay validation. Once optimization of the signal in the assay is complete, it is necessary to validate the assay. The criteria are similar to those that the researcher would apply to a filtration assay. They involve:

Perform control experiments using a cell line or tissue which is known not to express the receptor of interest.
Perform competitive binding curves with known drugs for the receptor of interest and compare IC50/Ki values.
Perform saturation binding experiments and compare Kd values. To obtain Kd values it is necessary to convert SPA counts to dpms. This can be achieved by measuring a sample which has radioisotope bound to the beads but no unbound radioactivity present, firstly as SPA counts and then in another counter standardized to give dpms for that radioisotope. 3H or 125I labeled PVT beads from the color quench correction kits (Amersham Codes TRKQ 7080 and RPAQ 4030 respectively) are convenient for this purpose.

It will not always be possible to apply all these criteria to any particular receptor assay.

Finally before analyzing colored samples, color quench correction curves should be installed.

EXAMPLES

Example 1: Materials and Methods

Preparation of Recombinant NR2F6—Human NR2F6 cDNA (a kind gift from John Ladias, Harvard University) was amplified by PCR using the PFX polymerase (Invitrogen) that possesses a proofreading 3'-5' exonuclease activity and provides higher fidelity of amplification than alternative polymerases. Primer sequences were selected that amplified the cDNA that encoded for amino acid residues 173-414 which contained the LBD of NR2F6. These amino acid residues can be found in SEQ ID No. 22. The amplicon was ligated in to the bacterial expression vector pGEX-4T-2 (Amersham Pharmacia Biotech) to produce the vector pGEX-LBDNR2F6 containing the ligand binding domain of human NR2F6 fused to glutathione S-transferase. Clones were verified to be error-free by sequencing. *Escherichia coli* BL-21 cells were transformed with pGEX-LBDNR2F6 plasmid DNA. Cells were cultured and induced with isopropyl-β-D-thiogalactopyranoside as described by the supplier. The cells were pelleted by centrifugation for 20 min at 2,000 rpm and the pellet was resuspended in 30 ml of phosphate-buffered saline containing 0.25 mM phenylmethylsulfonyl fluoride/1,000 ml of culture medium. Two passes through a French press were used to disrupt the cells, and cellular debris was removed by centrifugation at 10,000 rpm, 4° C. Recombinant pGEX-LBDNR2F6 was isolated batchwise using glutathione-Sepharose as described by the supplier (Amersham Pharmacia Biotech). Typically, 2 mg of pGEX-LBDNR2F6 at approximately 50% purity was obtained per liter of bacterial culture.

SPA Binding Assay—The binding assay was developed for use with microtiter plates (Dynex Technologies, catalog number 011-010-7905) using a total volume of 100 µl of assay buffer: 10 mM Tris-Cl, pH 7.2, 1 mM EDTA, 10% (w/v) glycerol, 10 mM sodium molybdate, 1 mM dithiothreitol, 0.5 mM phenylmethylsulfonyl fluoride, 2 µg/ml benzamidine, and 0.1% dry milk powder. Each bottle of protein A-yttrium silicate SPA beads (Amersham Pharmacia Biotech catalog number RPN143) was suspended in 25 ml of assay buffer but omitting the dry milk powder and adding sodium azide to a final concentration of 0.01%. [$^3H_2$]5-[4-[2-(5-metyl-2-phenyl-4-oxazolyl)-2-hydroxyethoxy]benzyl]-2,4-thiazolidinedione ([$^3H$]TZD), 21 Ci/mmol, was dissolved in ethanol and used at a final concentration of 10 nM. The recombinant GST-NR2F6 preparations were usually used at a dilution of 800× producing a final concentration of approximately 5 nM. Goat anti-GST antibodies were obtained from Amersham Pharmacia Biotech (catalog number 27-4577-01) and used at a 400-fold final dilution. The GST-NR2F6, goat anti-GST antibodies, and [$^3H$]TZD were diluted in assay buffer and combined in a total volume of 70 µl in the microtiter plate. Five µl of test compound was added so that the final concentration of Me$_2$SO did not exceed 2%. Following the addition of 25 µl of protein A-yttrium silicate SPA beads to each well, the plate was incubated at 15° C. for 24 h with shaking Radioactivity was quantified in a Packard Topcount scintillation counter.

Fluorescence quenching (FQ) analysis—All fluorescent spectra were recorded on F-2500 fluorescence spectrophotometer (Hitachi, Japan) equipped with 1.0 cm quartz cells. The widths of both the excitation and emission slits were set to 5 nm. Excitation wavelength of 280 nm was set based on the intrinsic property of tryptophan (Trp) fluorophore, and the emission spectra were recorded from 300 to 400 nm at 25° C. 51M LBDNR2F6 was mixed with different concentrations of troglitazone or test compounds for up to 30 min. Then sample was placed in a quartz cell and kept for 5 min in dark before measurements. All final spectra were corrected by deducting the buffer contribution, and the obtained results were the average of three parallel measurements.

Enzymatic NR2F6 assay: fluorescence polarization. Enzymatic NR2F6 assays were performed using the IMAP technology (MDS analytic Technologies). The desired test compound concentration was mixed with 50 nM LBD-NR2F6, 400 nM fluorescein labelled peptide and 1.7 M Troglitazone in 8 µL 20 mM Mes pH 6.5, 0.4 mM MgCl2, 0.4 mM MnCl2, 1 mM DTT, 0.01% NP40. After 60 min incubation reaction was stopped by adding IMAP binding solution and NR2F6 activity was quantified my measuring fluorescence polarization.

Surface plasmon resonance (SPR) technology-based binding and coactivator recruitment assays—Binding of troglitazone or test compounds to the LBD-NR2F6 recombinant protein was investigated by using surface plasmon resonance (SPR) technology-based Biacore 3000 instrument (GE Healthcare). Purified LBD-NR2F6 recombinant protein was immobilized on CM5 sensor chip by the standard primary amine coupling reaction, followed by the injection of different concentrations of troglitazone or test compounds to the chip. In the coactivator recruitment experiment, Bio-SCR1 was immobilized on SA chip. The pre-incubated LBD-NR2F6 with different concentrations of troglitazone or test compounds and 50 lM CDCA was injected onto the chip. All experiments were carried out at 25° C. with HBS-EP as running buffer at a constant flow of 30 lL/min. The equilibrium dissociation constant (KD) was achieved by fitting the data using 1:1 Langmuir binding model based on the BIAevaluation 3.1 software.

Radioactive Variant of the NR2F6 Ligand Binding Assay: Filtration assay—In a total volume of 100 µL, 50-µL recombinant LBD-NR2F6 receptor proteins (34 µg/µL, 1.7 µg protein/well) were incubated for 1 h at 37° C. under mild stirring (300 rpm) in assay buffer (50 mM TRIS, 5 mM MgCl2, 1 mM EDTA, 0.3% BSA; pH 7.4). In the saturation experiments (for the determination of Kd and Bmax values), increasing concentrations of [3H]-troglitazone were incubated in the absence (for total binding, TB) or presence of 10 µM troglitazone (for nonspecific binding, NSB). In the displacement experiments (for determination of Ki values), the recombinant LBD-NR2F6 receptor proteins were incubated with 0.6 nM [3H]-troglitazone and increasing concentrations of test compounds ($10^{-11}$ to $10^{-5}$ $^M$). The bound fraction was separated from the free radioligand by filtration using a Brandell 96-well harvester (Semat International, St. Albans, United Kingdom) under vacuum through a Filtermat A glass fiber filter (prewetted with buffer 50 mM TRIS, 5 mM MgCl2, 1 mM EDTA, 1% BSA; pH 7.4). Filters were washed 6× with wash buffer (50 mM TRIS, 5 mM MgCl2, 1 mM EDTA; pH 7.4) and dried for 1 h at 80° C. The retained radioactivity was measured with both the upper and bottom PMT tubes on the Wallac Trilux Counter (PerkinElmer Life Sciences/Wallac).

Fluorescent Variant of the NR2F6 Ligand Binding Assay—The NR2F6 ligand binding assay described here is a fluorescence variant that is based on the principle of reporter displacement. This assay is based on a known ligand that acts as a reporter probe that is distinctively designed to bind to the site of interest of NR2F6. The proximity between known ligand that acts as a reporter and the recombinant NR2F6 protein results in the emission of an optical signal. Fragments that bind to the same binding site are displacing the probe and causing signal loss. The displacement assay is a homogeneous method. Due to the nature of the optical signal, interference by the optical properties of compounds or fragments is very limited. The reporter displacement assay was performed in a volume of 84, per well within a 384 well low volume plate. About 2 nM LBD-NR2F6 was mixed with a 29 nM Troglitazone site specific reporter probe in 20 mM Mops pH 7.0, 1 mM DTT, 0.01% Tween20. After 60 min incubation test compounds were added at the desired concentration. Displacement of the reporter probe was measured either after 60 min incubation or continuously over time. The signal for full probe binding was measured in the absence of compound and the signal for complete reporter displacement was quantified in the absence of LBD-NR2F6.

Radioactive Variant of the NR2F6 Ligand Binding Assay using the ScreenReady™ Targets/Flashplate format—The ScreenReady™ Targets were basic Flashplates® coated with the LBD-NR2F6 receptors purified from E Coli. Each well contained $3.12 \times 10^{-15}$ mol LBD-NR2F6 receptor proteins. The LBD-NR2F6 receptor proteins were incubated with the corresponding reagents for 3 h at 21° C. under mild stirring (300 rpm) in assay buffer (50 mM TRIS, 5 mM MgCl2, 1 mM EDTA, 0.3% BSA; pH 7.4) with a final volume of 20 µL. In the saturation experiments, increasing concentrations of [3H]-troglitazone were incubated in the absence (for true binding) or presence of 10 µM troglitazone (for nonspecific binding). In the displacement experiments, the LBD-NR2F6 receptor proteins were incubated with 0.6 nM [3H]-troglitazone and increasing concentrations of test compounds. The Flashplates® were measured with the upper PMT tubes only on the Wallac Trilux Counter.

WGA-coated Flashplates®—The WGA-coated Flashplates® were basic flashplates of which the interior of the wells was coated with WGA. The WGA Flashplates® were coated with recombinant LBD-NR2F6 produced as described above. These membranes contained $0.8 \times 10^{-12}$ mol recombinant LBD-NR2F6 receptors/mg protein and 1.02 mg protein/mL.

After a pre-coating period of 1 h at 4° C. with pre-coating buffer (50 mM TRIS, 5 mM MgCl2, 1 mM EDTA, 1% BSA; pH 7.4), the wells were incubated overnight at 4° C. with an 80-μL protein suspension (34 ng/μL, 2.72 μg protein/well) per well in binding buffer containing 0.3% BSA under mild stirring (300 rpm). After aspiration, the recombinant LBD-NR2F6 protein was incubated for 3 h at 21° C. under mild stirring (300 rpm) in assay buffer (50 mM TRIS, 5 mM MgCl2, 1 mM EDTA, 0.3% BSA; pH 7.4) with a final volume of 60 μL. In the saturation experiments, increasing concentrations of [3H]-Troglitazone was incubated in the absence (for true-binding) or presence of 10 μM troglitazone (for non-specific binding). In the displacement experiments, the membranes were incubated with 0.6 nM [3H]-Troglitazone and increasing concentrations of test compounds competing ligands ($10^{-11}$ to $10^{-5}$ M). The Flashplates® were measured with the upper PMT tubes only on the Wallac Trilux Counter. The Flashplates® were counted again after overnight incubation and after washing twice with phosphate-buffered saline (PBS).

Data analysis—The binding data were evaluated using Prism® v3.0 (Graphpad Software, Inc., San Diego, Calif.) with a nonlinear, 1-site binding equation for the saturation experiments to obtain the Kd and Bmax values. For the displacement experiments, a nonlinear, 1-site competition equation as a curve-fitting procedure was used to obtain IC50 values. The transformation of IC50 values into Ki values was performed using the Cheng-Prusoff equation. The Z' factor was calculated using the formula described by: Z'=1−(3STB+3SNSB)/|TB−XNSB|. The signal dynamic range was calculated using the average total binding as the maximum value (XTB) and the average nonspecific binding as the minimum value (XNSB). The standard deviations were calculated from the triplicate values so that the Z' factor per experiment (plate) could be calculated. The Z' factor of repeated experiments (multiple plates) was then averaged to determine the Z' factor per assay.

Example 2: Characterization of the SPA Assay

We determined the background of the assay, defined as the counts/minute obtained in 100× excess of unlabeled TZD ligand. The background of the assay was determined to be was less than 50 cpm. We determined that at concentrations of 10 nM [3H]TZD the total counts/minute obtained were approximately 600, providing a 12-fold window of specific binding activity. We produced a saturation curve by using increasing concentrations of the [3H]TZD. These data were used to generate a Scatchard plot, that showed a single population of binding sites. From the number of binding sites obtained from the Scatchard plot, and from the purity of the GST-LBDNR2F6 preparation as determined by SDS-gel electrophoresis, we estimate that >20% of the protein was active in binding. Known thiazolidinedione including TZD, BRL49653, and CS-045, were titrated in the SPA assay. IC50 values were determined. These IC50 values cover 2 orders of magnitude and agree well with previously published binding activities determined using dextran/gelatin-coated charcoal to separate bound from free ligand. Furthermore, the rank order of these compounds is reflected in both transactivation assays and in their in vivo glucose lowering activity.

Example 3: REG002376 is a Novel NR2F6 Ligand

Using the SPA assay approach, a number of small molecules were screened. REG002376 was shown to be a potent NR2F6 ligand. Thus, titration of this compound revealed an apparent IC50 of 70 nM.

Example 4: [3H]TZD Cannot Displace REG002376 in the SPA Assay

The SPA assay was used to determine whether a TZD could displace REG002376 from NR2F6. The experiment was designed to also ensure that NR2F6 binding activity could still be detected after 48 h. Thus, recombinant receptor was incubated with 10 nM [3H]TZD and submaximal amounts of either REG002376 or unlabeled TZD. After 24 h, the amount of [3H]TZD was increased to 50 nM. Under these conditions, the amount of specific binding should increase with time as the system progresses toward equilibrium, but only if binding sites are still available. As seen in, this only occurs with the samples preincubated with either 15 or 20 nM TZD. Those samples preincubated with either 150 or 300 nM REG002376 did not exhibit an increase in specific counts, suggesting that there were no free binding sites available to be occupied by the increased amount of [3H]TZD. This would be expected if REG002376 was a covalent ligand, since binding equilibrium would not be achieved. These results were confirmed by preincubation of NR2F6 with REG002376 at a maximally effective concentration of 4 μM. Under these conditions, no [3H]TZD binding activity could be detected after 24 h, while a second sample incubated in parallel with vehicle alone retained binding activity.

Example 5: Identifying Compounds During Hit-to-Lead Drug Discovery. Compound REG001793, REG001703 and REG001743 Activates NR2F6

On the basis of the structural similarity we selected 10 small molecules with similar chemical structures to compound REG002376 to test for binding to NR2F6. Initially, REG002376 was compared with troglitazone, a known ligand. To determine whether REG002376 was directly binding of to NR2F6, a scintillation proximity assay was performed, using the methods described above using [3H]-troglitazone as the known ligand. Both REG002376 and compounds REG001793 REG001703 and REG001743 caused a dose-dependent displacement of [3H]-troglitazone, indicating that in addition to REG002376, REG001793, REG001703 and REG001743 binds directly to NR2F6. Moreso, we determined not only that compounds REG001793, REG001703 and REG001743 could bind, but also that they were able to bind with higher affinity than compound REG002376. These compounds were determined to be compounds that directly bound to NR2F6 and were selected for further investigation in the hit-to-lead process.

Example 6: Identifying Compounds Using a Fluorescence Quenching (FQ) Format

Given the two Tryptophan residues of W216 and W239 contained in the ligand binding domain of NR2F6, intrinsic fluorescence quenching (FQ) approach was used for examination of LBD-NR2F6's ability to bind to troglitazone and compounds REG002376, REG001793, REG001703 and REG001743. In the assay, different concentrations of troglitazone or test compounds were incubated with LBD-NR2F6 (5 lM), and intrinsic fluorescence spectra were obtained. We observed that, LBD-NR2F6 displayed maximal fluorescence at 337 nm, and that the test compounds had no fluorescence at this wavelength. Treatment of both the test compounds REG002376, REG001793, REG001703 and REG001743 and troglitazone caused a quench of fluorescence intensity of LBD-NR2F6 in a dose-dependent manner, indicative of the binding of the compounds REG001793, REG001703 and REG001743 and troglitazone to LBD-NR2F6. We did not observe this when test compounds determined by SPA as not being able to bind to the ligand binding domain of NR2F6 were used, specifically REG002473, REG001648, REG001902, REG001311, REG001998, REG001513, REG003483, REG001897 were tested.

Example 7: Identifying Compounds Using a Surface Plasmon Resonance (SPR) Format

To inspect the binding and kinetic features of troglitazone as well as test compounds REG001793, REG001703, REG001743, REG002473, REG001648, REG001902, REG001311, REG001998, REG001513, REG003483, REG001897 binding to LBD-NR2F6, SPR-technology based Biacore 3000 was used. In the assay, the purified NR2F6-LBD was immobilized on CM5 chip according to the standard amine-coupling wizard, followed by the injections of troglitazone or the test compounds in different concentrations to the chip. The association (kon), dissociation (koff) rate constants and the dissociation equilibrium constant (1(D)) were thus obtained by fitting the sensorgrams with a 1:1 (Langmuir) binding fitting model. The kinetic results were noted. As demonstrated, troglitazone, REG001793, REG001703, REG001743 bound to NR2F6-LBD with a higher binding affinity than it did to test compounds REG002473, REG001648, REG001902, REG001311, REG001998, REG001513, REG003483, REG001897. We determined that binding to the test compound REG001793 was highest in the cohort of chemicals tested, as indicated by the determined KD value (5.1 µM) of REG001793 binding to LBD-NR2F6 based on this assay.

Example 8: Screening Using the Fluorescent Variant of the NR2F6 Ligand Binding Assay 170 test compounds from Regen BioPharma's collection of small molecules (obtained from various vendors including Enamime, Vitas M. Labs, Chembridge and others), were screened in triplicates against the LBD-NR2F6 protein using the reporter displacement assay system reported. Recombinant LBD-NR2F6 was incubated with a reporter probe that was specifically designed to bind to the ligand-binding domain of NR2F6. There—after 2 mM of an individual test compound was added per well of a 384 well screening plate and probe displacement was measured. On each screening plate the signal corresponding to 100% (absence of LBD-NR2F6) and 0% (absence of competing test compound) reporter displacement was measured in six wells, respectively. Assay stability was controlled by plotting signals for 100% and 0% reporter displacement for each screening plates. In addition assay significance was controlled by calculating the z prime for each screening plate. The z prime values for all screening plates were above 0.68 demonstrating the high significance of the screen. The z prime value for total screen considering all screening plates was calculated to be 0.72.

Test compounds that bound to the LBD binding site of NR2F6 were identified by quantifying reporter probe displacement and the hit rate was calculated grouped by degree of reporter displacement. Inspection of the structures of all fragments with more than 50% probe displacement resulted in a list of 4 fragments for further characterization. For these fragments the IC50 values were measured using the Fluorescent Variant of the NR2F6 Ligand Binding Assay displacement assay and in addition a luciferase based NR2F6 assay. In order to measure also the IC50 value of fragments with very low affinities a fragment concentration of up to 22.61 mM was used. For the NR2F6 Ligand Binding Assay the reporter probe concentration was adjusted to its own Kd value. Thus, according to the Cheng Prusoff equation in both assays the resulting IC50 values equal two times the Kd value and are directly comparable. From the 4 test compounds that hit positively from the primary screening effort, 3 fragments could be verified as NR2F6 binders by measuring a valid IC50 curve with the NR2F6 Ligand Binding Assay.

Example 9: Screening Using the Radioactive Variant of the NR2F6 Ligand Binding Assay: Filtration Assay Literature reports incubation temperatures at 37° C., 25° C., or room temperature mostly for 30 or 60 min, and therefore various incubation conditions were tested to optimize the filtration assay in a 96-well plate format suitable for screening. First, incubations at 21° C. with increasing incubation times (15-160 min) were tested. The ratio between the TB and the NSB was calculated. An incubation time of 60 min was required to reach a binding equilibrium. This equilibrium, characterized by a TB/NSB ratio of 8.3, remained constant for at least 160 min of incubation. To investigate the effect of temperature on the binding characteristics, further experiments were carried out under various incubation conditions (1 h at 21° C., 1 h at 37° C., and overnight at 4° C.). The same TB/NSB ratios were obtained for the incubations at 21° C. as in the previous experiment. The TB/NSB ratio increased both with temperature (1 h, 37° C.) and with duration of the incubation (overnight, 4° C.). The Kd values obtained from the saturation experiments remained stable under the different conditions. Also, the Ki values obtained in the displacement.

Experiments for the test compounds were consistent under the various incubation conditions. Equilibrium was reached after 1 h of incubation and remained stable even when left overnight at 4° C. Notably, we observed that an overnight incubation at 4° C. significantly decreases NSB, leading to a high TB/NSB ratio. The Kd values obtained for [3H]-Troglitazone are in agreement with results previously reported in literature. The obtained Ki values for the test compounds also fit within the anticipated Ki values based on a priori knowledge of their binding characteristics. A saturation curve and displacement curve were generated. The average Z' factor obtained for this assay is 0.6, implicating that the assay is suitable for screening. We hence screened 170 compounds from our Regen BioPharma's collection of small molecules and observed binding of 3 compounds. A disadvantage of this assay is that it is a heterogeneous assay and that a filtration step is necessary to separate bound from unbound radioactive ligand. Subsequently, it is necessary to add a liquid scintillation cocktail to amplify the signal and seal the filter for protection, making this filtration assay labor intensive. In addition, a considerable amount of radioactive liquid waste is produced.

Example 10: Screening Using the Radioactive Variant of the NR2F6 Ligand Binding Assay: ScreenReady™ Target Saturation and competition experiments were carried out to determine if the criteria of the manufacturer could be met. The apparent Kd value of [3H]-troglitazone and the Bmax value observed was 0.65 nM and 438 fmol/mg LBD-NR2F6 protein, respectively. Both values were close to the values given by the manufacturer, 1.05 nM and 480 fmol/mg membrane protein, respectively. Different incubation times were investigated in addition to the 2 h suggested by the manufacturer. The same plate with displacement experiments of troglitazone and test compounds was measured after 2 and 3 h and subsequently every 2 h for up to 23 h. The apparent average Ki values obtained for troglitazone were 10.6±0.9 nM and various for values for respective test compounds. We observed that a higher total binding is obtained after 3 h of incubation, whereas the nonspecific binding remained the same, which results in a better TB/NSB ratio. We also observed that the high signal for TB remained stable for about 7 h. After 7 h, the TB signal started to decrease slowly, and after 17 h, the TB signal was back to the observed signal after 2 h of incubation. Because the NSB remained the same during the 23 h, the TB/NSB ratio follows the same trend line and was highest after 7 and 9 h of incubation. An incubation time of 3 h was selected for screening because a good TB/NSB ratio of 5.3 was obtained with still an acceptable incubation time. For both price and environmental reasons, the use of radioligand should be limited. Therefore, different incubation volumes were tested. Saturation experiments were carried out in a final volume of 20, 25 (suggested by manufacturer), and 30 µL. Displacement experiments were carried out in a final volume of 20, 25, 40, and 100 µL. We observed that the percentage binding and the shape of the curves are not affected. Also, parameters such as Kd, Bmax, and Ki values and the TB/NSB ratio calculated from these graphs were not affected by different incubation volumes. Interestingly, the apparent Ki values for troglitazone and the test compounds tested, as well as the apparent Kd value of [3H]-troglitazone, were significantly higher in the ScreenReady™ Target assay than in the filtration assay. A possible explanation for this could be that the receptors are attached to the surface of the well instead of being in free solution. This surface attachment may modulate their conformational liberty, resulting in decreased receptor accessibility. The average Z' factor obtained with the ScreenReady™ Target is 0.8. For screening purposes, an incubation volume of 20 µL is sufficient. It is literally a homogeneous assay with a mix-and-measure principle. These plates are safe to work with because the radioactivity is added in small volumes, sealed in the plate, and discarded as a whole. Due to the small volume and the nature of the assay, little radioactive waste is produced.

Example 11: Screening Using the Radioactive Variant of the NR2F6 Ligand Binding Assay: ScreenReady™ Target To reduce the NSB, BSA was used. First, the WGA Flashplates® were precoated with 1% BSA before incubating the plates with membranes; second, the percentage BSA in the binding buffer with the membranes was increased. We shows that the combination of precoating the WGA plates with 1% BSA and adding 0.3% BSA in the binding buffer results in a significant improvement of the specific binding (dark bars), with a TB/NSB ratio of 3. Attempts to further increase this ratio by decreasing the amounts of membranes were unsuccessful; TB decreased, but the NSB remained the same, confirming high levels of a specific binding of [3H]-troglitazone to the WGA. The optimal assay conditions are as follows: precoating the WGA Flashplate® with a 1% BSA solution for 1 h, followed by coating the plate with an 80-µL membrane suspension (34 ng/µL) in binding buffer containing 0.3% BSA. The actual incubation with 0.6 nM [3H]-Troglitazone and test compound is carried out in a final volume of 60 µL.

The saturation and displacement experiments carried out with troglitazone and test compounds in the WGA-coated Flashplates® still show a high NSB after 3 h of incubation. The TB/NSB ratio here is 2. Overnight incubation (16 h) of the same plate causes a decrease in the NSB, but it remains too high, resulting in a TB/NSB ratio of 2.3. Because of the high nonspecific binding, it is difficult to determine the saturation level (100% occupation of the receptors) and thus the Bmax that results in a considerable variation, especially after 3 h of incubation. The apparent Kd values obtained with the WGA Flashplate® experiments showed acceptable variation. The higher variation seen in this assay is probably due to the extra step in which the Flashplates® have to be coated "in-house" with recombinant LBD-NR2F6 protein. However, a major improvement was achieved when the plates were washed twice with PBS. The NSB decreased substantially, and resulted in a TB/NSB ratio of 10 and a high Z' factor of 0.8, which makes the assay just as good as previously described assays. Also, the apparent Ki values obtained for troglitazone and test compound with this assay were similar to the results obtained with the ScreenReady™ Target. Although washing greatly improves the WGA Flashplate® assay, it introduces yet an additional handling step and thus eliminates the speed and ease of a homogeneous assay. Indeed, in our experience, the development and optimization of the LBD-NR2F6 receptor assay on the WGA Flashplate® were more time-consuming than the other assays due to the various handling steps involved, nevertheless, we optimized the assay and used it to screen the Regen BioPharma collection of 170 small molecules and observing binding of 3 test compounds.

```
Sequence Listing

NCBI Reference Sequence: NM_005234.3
>gi|46411186|ref|NM_005234.3|Homo sapiens
nuclear receptor subfamily 2, group F,
member 6 (NR2F6), mRNA
                                                           SEQ ID NO: 1
GTGCAGCCCGTGCCCCCCGCGCGCCGGGGCCGAATGCGCGCCGCGTA

GGGTCCCCCGGGCCGAGAGGGGTGCCCGGAGGGAAGAGCGCGGTGGG

GGCGCCCCGGCCCCGCTGCCCTGGGGCTATGGCCATGGTGACCGGCG

GCTGGGGCGGCCCCGGCGGCGACACGAACGGCGTGGACAAGGCGGGC

GGCTACCCGCGCGCGGCCGAGGACGACTCGGCCTCGCCCCCCGGTGC

CGCCAGCGACGCCGAGCCGGGCGACGAGGAGCGGCCGGGGCTGCAGG
```

Sequence Listing

```
TGGACTGCGTGGTGTGCGGGGACAAGTCGAGCGGCAAGCATTACGGT
GTCTTCACCTGCGAGGGCTGCAAGAGCTTTTTCAAGCGAAGCATCCG
CCGCAACCTCAGCTACACCTGCCGGTCCAACCGTGACTGCCAGATCG
ACCAGCACCACCGGAACCAGTGCCAGTACTGCCGTCTCAAGAAGTGC
TTCCGGGTGGGCATGAGGAAGGAGGCGGTGCAGCGCGGCCGCATCCC
GCACTCGCTGCCTGGTGCCGTGGCCGCCTCCTCGGGCAGCCCCCCGG
GCTCGGCGCTGGCGGCAGTGGCGAGCGGCGGAGACCTCTTCCCGGGG
CAGCCGGTGTCCGAACTGATCGCGCAGCTGCTGCGCGCTGAGCCCTA
CCCTGCGGCGGCCGGACGCTTCGGCGCAGGGGGCGGCGCGGCGGGCG
CGGTGCTGGGCATCGACAACGTGTGCGAGCTGGCGGCGCGGCTGCTC
TTCAGCACCGTGGAGTGGGCGCGCCACGCGCCCTTCTTCCCCGAGCT
GCCGGTGGCCGACCAGGTGGCGCTGCTGCGCCTGAGCTGGAGCGAGC
TCTTCGTGCTGAACGCGGCGCAGGCGGCGCTGCCCCTGCACACGGCG
CCGCTACTGGCCGCCGCCGGCCTCCACGCCGCGCCTATGGCCGCCGA
GCGCGCCGTGGCTTTCATGGACCAGGTGCGCGCCTTCCAGGAGCAGG
TGGACAAGCTGGGCCGCCTGCAGGTCGACTCGGCCGAGTATGGCTGC
CTCAAGGCCATCGCGCTCTTCACGCCCGACGCCTGTGGCCTCTCAGA
CCCGGCCCACGTTGAGAGCCTGCAGGAGAAGGCGCAGGTGGCCCTCA
CCGAGTATGTGCGGGCGCAGTACCCGTCCCAGCCCCAGCGCTTCGGG
CGCCTGCTGCTGCGGCTCCCCGCCCTGCGCGCGGTCCCTGCCTCCCT
CATCTCCCAGCTGTTCTTCATGCGCCTGGTGGGGAAGACGCCCATTG
AGACACTGATCAGAGACATGCTGCTGTCGGGGAGTACCTTCAACTGG
CCCTACGGCTCGGGCCAGTGACCATGACGGGGCCACGTGTGCTGTGG
CCAGGCCTGCAGACAGACCTCAAGGGACAGGGAATGCTGAGGCCTCG
AGGGGCCTCCCGGGGCCCAGGACTCTGGCTTCTCTCCTCAGACTTCT
ATTTTTTAAAGACTGTGAAATGTTTGTCTTTTCTGTTTTTTAAATGA
TCATGAAACCAAAAAGAGACTGATCATCCAGGCCTCAGCCTCATCCT
CCCCAGGACCCCTGTCCAGGATGGAGGGTCCAATCCTAGGACAGCCT
TGTTCCTCAGCACCCCTAGCATGAACTTGTGGGATGGTGGGGTTGGC
TTCCCTGGCATGATGGACAAAGGCCTGGCGTCGGCCAGAGGGGCTGC
TCCAGTGGGCAGGGGTAGCTAGCGTGTGCCAGGCAGATCCTCTGGAC
ACGTAACCTATGTCAGACACTACATGATGACTCAAGGCCAATAATAA
AGACATTTCCTACCTGCA
```

*Mus musculus* nuclear receptor subfamily 2, group F, member 6 (Nr2f6), mRNA NCBI Reference Sequence: NM_010150.2
>gi|112807198|ref|NM_010150.2|*Mus musculus* nuclear receptor subfamily 2, group F, member 6 (Nr2f6), mRNA

SEQ ID NO: 2

```
GGCGCCGATGGAACGCGGGTGTCAGGCCGGCCGCAGCGCGGGGCCGG
CGGCGAGCGCCAGGGCGAGGCCGAGGCTCGGGCCCAGGCGCAGGCCG
```

Sequence Listing

```
AGGCCGGCCGCGCGAGCGCTCGGCGGGGAGACGATCCAGGGAAGGCC

GCGGGTCGCACTCTCCACTCAGCTCTATCGCCTGGACCTCTGCGATT

ACGGCCGGGCGCGCGGCGTGCGGGACTCCGGGTCTCCGACGCGCG

CTCCCGCCGCCCCTCCCCCCTCGCCGCGTAACTTGCGGCCAAAGTTT

CCCCCCGGGCTCGGGGGCGCCCGCGCGCGCTCGGATGGTGAGCCACT

AAGTTGGCCTGGGCGGCGGGGCCGGGCCATGGCCCCCGCGACGCTAC

CGGGTCCCCAGGACTCCGGACCACGGGACCTGGGCGCCCCAGACTCG

CGCCTCTAGCGCGCCCCCGTCGACCGCGGGCACGCGTGGGAAAGTTG

GCCTGGAACCGGCCCGACCAGTTCCTGCCTGGCGCGCGGACCGGCCG

CAGGAAGTTGCCGCAAAACTTTTTTCAGGGGGTGTGCGACCGGAGC

CCCCCGAGAGCGCGGGCTGCATGCGCCCGGGGTAGCCGGGTCCCTCT

CGGGTCGCCAGGCGTGCCCAGAGGGGACGGACTCGTCCCGGGGCGTA

CCGGCCCCGCTGTCTCCGGGGCTATGGCCATGGTGACCGGTGGCTGG

GGCGACCCCGGAGGCGACACGAACGGCGTGGACAAGGCTGGTGGGAG

CTACCCACGCGCGACCGAGGACGATTCGGCGTCACCTCCCGGGGCGA

CCAGCGACGCGGAGCCGGGCGACGAGGAGCGTCCGGGGTTGCAGGTG

GACTGCGTGGTGTGCGGGGACAAGTCCAGTGGAAAGCATTACGGCGT

GTTCACCTGCGAGGGCTGCAAGAGTTTCTTCAAGCGCAGCATCCGCC

GCAATCTCAGCTACACCTGCCGGTCCAACCGTGACTGTCAGATTGAT

CAGCACCACCGGAACCAGTGTCAGTACTGTCGGCTCAAGAAGTGCTT

CCGGGTGGGCATGCGCAAGGAGGCCGTGCAGCGAGGCCGCATCCCGC

ATGCGCTCCCCGGTCCAGCGGCCTGCAGTCCCCCGGGCGCGACGGGC

GTCGAACCTTTCACGGGCCGCCAGTGTCCGAGCTGATTGCGCAGCT

GCTGCGTGCTGAGCCCTACCCCGCGGCCGGACGCTTTGGTGGCGGCG

GCGCTGTACTGGGCATCGACAACGTGTGCGAGTTGGCGGCACGCCTG

CTGTTCAGCACGGTCGAGTGGGCCCGCCACGCGCCCTTCTTCCCCGA

GCTGCCGGCCGCCGACCAGGTGGCGCTGCTGCGGCTCAGCTGGAGTG

AGCTCTTCGTGCTGAACGCGGCGCAGGCGGCGCTGCCGCTGCATACG

GCACCGCTGCTGGCCGCCGCGGGGTTGCATGCCGCGCCCATGGCAGC

CGAGCGGGCCGTGGCCTTCATGGACCAGGTGCGTGCCTTCCAGGAGC

AGGTGGACAAGCTGGGCCGCCTGCAGGTGGATGCTGCGGAGTACGGC

TGCCTCAAGGCCATCGCGCTCTTCACGCCTGATGCCTGTGGCCTTTC

TGACCCAGCCCATGTGGAGAGCCTGCAGGAGAAGGCACAGGTGGCCC

TCACCGAGTATGTGCGTGCCCAGTACCCATCGCAGCCCCAGCGCTTT

GGGCGTCTGCTGCTGCGGCTGCCAGCCCTGCGTGCTGTGCCCGCATC

CCTCATCTCCCAGCTCTTCTTCATGCGCCTGGTGGGCAAGACACCCA

TCGAGACCCTCATCCGGGACATGCTTCTGTCAGGGAGCACCTTTAAC

TGGCCCTATGGCTCGGGCTAGTGATAGTCACCTTCCAGGACATACAT

GGAAACTGGGGCCTTGTGGGGACCCTGGGGATCAGGGCCCCAGCTTC
```

```
TCTTTTGAGACTGATTTCTTTTTTTAAAGACTGTGAAATGTTTGTTT

TGTTTTATTTTTTAAATAATCATGAAACCAAAAAGATTTGGATCTCC

CAGGCCTTGTCCTGGCAGACCTTCAACAGTCTGGAGCCAGCATGCTG

ATGCCTCTGGTGTCATGGGTATCTGGAAAGGCCACTGCAGCTAGGCA

GGAGTACTATGGGCCAGGAGGATCCCCTGGATACATGGTCCACGGAG

GGCACCATGGGATGATGAAAACCTGGCCAATAATAAAGGTATTCCCT

TACTTGGTC
```

Protein Sequence of human NR2F6
>gi|23503053|sp|P10588.2|NR2F6_HUMAN RecName:
Full = Nuclear receptor subfamily 2 group F
member 6; AltName: Full = V-erbA-related
protein 2; Short = EAR-2                                SEQ ID NO: 3

```
MAMVTGGWGGPGGDTNGVDKAGGYPRAAEDDSASPPGAASDAEPGDE

ERPGLQVDCVVCGDKSSGKHYGVFTCEGCKSFFKRSIRRNLSYTCRS

NRDCQIDQHHRNQCQYCRLKKCFRVGMRKEAVQRGRIPHSLPGAVAA

SSGSPPGSALAAVASGGDLFPGQPVSELIAQLLRAEPYPAAAGRFGA

GGGAAGAVLGIDNVCELAARLLFSTVEWARHAPFFPELPVADQVALL

RLSWSELFVLNAAQAALPLHTAPLLAAAGLHAAPMAAERAVAFMDQV

RAFQEQVDKLGRLQVDSAEYGCLKAIALFTPDACGLSDPAHVESLQE

KAQVALTEYVRAQYPSQPQRFGRLLLRLPALRAVPASLISQLFFMRL

VGKTPIETLIRDMLLSGSTFNWPYGSGQ
```

Protein Sequence of NR2F6 mus musculus
>gi|112807199|ref|NP_034280.2|nuclear
receptor subfamily 2 group F member 6
[Mus musculus]                                           SEQ ID NO: 4

```
MAMVTGGWGDPGGDTNGVDKAGGSYPRATEDDSASPPGATSDAEPGD

EERPGLQVDCVVCGDKSSGKHYGVFTCEGCKSFFKRSIRRNLSYTCR

SNRDCQIDQHHRNQCQYCRLKKCFRVGMRKEAVQRGRIPHALPGPAA

CSPPGATGVEPFTGPPVSELIAQLLRAEPYPAAGRFGGGGAVLGIDN

VCELAARLLFSTVEWARHAPFFPELPAADQVALLRLSWSELFVLNAA

QAALPLHTAPLLAAAGLHAAPMAAERAVAFMDQVRAFQEQVDKLGRL

QVDAAEYGCLKAIALFTPDACGLSDPAHVESLQEKAQVALTEYVRAQ

YPSQPQRFGRLLLRLPALRAVPASLISQLFFMRLVGKTPIETLIRDM

LLSGSTFNWPYGSG
```

(human siRNA)                                            SEQ ID NO: 18
```
GCCGUCUCAAGAAGUGCUU
```

(human siRNA)                                            SEQ ID NO: 19
```
CAUUGAGACACUGAUCAGA
```

(human siRNA)                                            SEQ ID NO: 20
```
GCAAGCAUUACGGUGUCUU
```

(human siRNA)                                            SEQ ID NO: 21
```
CCCCUAGCAUGAACUUGUG
```

Sequence Listing (mus shNR2F6.1)

SEQ ID NO: 5

GAT CCG CAT TAC GGC GTG TTC ACC TTC AAG AGA GGT GAA CAC GCC GTA ATG CTT TTT TCT AGA G (mus shNR2F6.2)

SEQ ID NO: 6

GAT CCG CAA CCG TGA CTG TCA GAT TAA GTT CTC TAA TCT GAC AGT CAC GGT TGT TTT TCT AGA G (mus shNR2F6.3)

SEQ ID NO: 7

GAT CCG TGT CCG AGC TGA TTG CGC ATT CAA GAG ATG CGC AAT CAG CTC GGA CAT TTT TCT AGA G (human shNR2F6.1)

SEQ ID NO: 8

GAT CCG CAT TAC GGT GTC TTC ACC TTC AAG AGA GGT GAA GAC ACC GTA ATG CTT TTT TCT AGA G (human shNR2F6.2)

SEQ ID NO: 9

GAT CCG CCT CTG GAC ACG TAA CCT ATT CAA GAG ATA GGT TAC GTG TCC AGA GGT TTT TCT AGA G

Primers
Human NR2F6:
Fwd:

SEQ ID NO: 10

5'-TCTCCCAGCTGTTCTTCATGC-3'

Revs:

SEQ ID NO: 11

5'-CCAGTTGAAGGTACTCCCCG-3'

Human GAPDH:
Fwd:

SEQ ID NO: 12

5'-GGCCTCCAAGGAGTAAGACC-3'

Revs:

SEQ ID NO: 13

5'-AGGGGTCTACATGGCAACTG-3'.

3' end Mus NR2F6:
Fwd:

SEQ ID NO: 14

5'-CCTGGCAGACCTTCAACAG-3'

Revs:

SEQ ID NO: 15

5'-GATCCTCCTGGCCCATAGT-3'

3' end Mus L32:
Fwd:

SEQ ID NO: 16

5'-GCCATCAGAGTCACCAATCC-3'

Revs:

SEQ ID NO: 17

5'-AAACATGCACACAAGCCATC-3'

Protein Sequence of human NR2F6
>gi|23503053|sp|P10588.2|NR2F6_HUMAN RecName:
Full = Nuclear receptor subfamily
2 group F member 6; AltName: Full = V-erbA-
related protein 2; Short = EAR-2

SEQ ID NO: 22

173  LLRAEPYP

181  AAAGRFGAGG GAAGAVLGID NVCELAARLL FSTVEWARHA PFFPELPVAD QVALLRLSWS

241  ELFVLNAAQA ALPLHTAPLL AAAGLHAAPM AAERAVAFMD QVRAFQEQVD KLGRLQVDSA

```
          -continued
                   Sequence Listing

301   EYGCLKAIAL FTPDACGLSD PAHVESLQEK AQVALTEYVR AQYPSQPQRF GRLLLRLPAL

361   RAVPASLISQ LFFMRLVGKT PIETLIRDML LSGSTFNWPY GSGQ
```

REFERENCES

1. Ichim, C. V. and R. A. Wells, First among equals: The cancer cell hierarchy. Leukemia and Lymphoma (in press), 2006.
2. Bonnet, D. and J. E. Dick, Human acute myeloid leukemia is organized as a hierarchy that originates from a primitive hematopoietic cell. Nat Med, 1997. 3(7): p. 730-7.
3. Singh, S. K., et al., Identification of a cancer stem cell in human brain tumors. Cancer Res, 2003. 63(18): p. 5821-8.
4. Singh, S. K., et al., Identification of human brain tumour initiating cells. Nature, 2004. 432(7015): p. 396-401.
5. Al-Hajj, M., et al., Prospective identification of tumorigenic breast cancer cells. Proc Natl Acad Sci USA, 2003. 100(7): p. 3983-8.
6. Reya, T., et al., A role for Wnt signalling in self-renewal of haematopoietic stem cells. Nature, 2003. 423(6938): p. 409-14.
7. Stier, S., et al., Notch1 activation increases hematopoietic stem cell self-renewal in vivo and favors lymphoid over myeloid lineage outcome. Blood, 2002. 99(7): p. 2369-78.
8. Karlsson, G., et al., Smad4 is critical for self-renewal of hematopoietic stem cells. J Exp Med, 2007. 204(3): p. 467-74.
9. Schnabel, C. A., Y. Jacobs, and M. L. Cleary, HoxA9-mediated immortalization of myeloid progenitors requires functional interactions with TALE cofactors Pbx and Meis. Oncogene, 2000. 19(5): p. 608-16.
10. Thorsteinsdottir, U., et al., Overexpression of the myeloid leukemia-associated Hoxa9 gene in bone marrow cells induces stem cell expansion. Blood, 2002. 99(1): p. 121-9.
11. Thorsteinsdottir, U., et al., Overexpression of HOXA10 in murine hematopoietic cells perturbs both myeloid and lymphoid differentiation and leads to acute myeloid leukemia. Mol Cell Biol, 1997. 17(1): p. 495-505.
12. Sauvageau, G., et al., Overexpression of HOXB4 in hematopoietic cells causes the selective expansion of more primitive populations in vitro and in vivo. Genes Dev, 1995. 9(14): p. 1753-65.
13. Lessard, J. and G. Sauvageau, Bmi-1 determines the proliferative capacity of normal and leukaemic stem cells. Nature, 2003. 423(6937): p. 255-60.
14. Park, I. K., et al., Bmi-1 is required for maintenance of adult self-renewing haematopoietic stem cells. Nature, 2003. 423(6937): p. 302-5.
15. Ernst, P., et al., Definitive hematopoiesis requires the mixed-lineage leukemia gene. Dev Cell, 2004. 6(3): p. 437-43.
16. Heyworth, C., et al., A GATA-2/estrogen receptor chimera functions as a ligand-dependent negative regulator of self-renewal. Genes Dev, 1999. 13(14): p. 1847-60.
17. Zeng, H., et al., Transcription factor Gfi1 regulates self-renewal and engraftment of hematopoietic stem cells. Embo J, 2004. 23(20): p. 4116-25.
18. Steidl, U., et al., Essential role of Jun family transcription factors in PU.1 knockdown-induced leukemic stem cells. Nat Genet, 2006. 38(11): p. 1269-77.
19. Iwasaki, H., et al., Distinctive and indispensable roles of PU.1 in maintenance of hematopoietic stem cells and their differentiation. Blood, 2005. 106(5): p. 1590-600.
20. White, J. R. and K. Weston, Myb is required for self-renewal in a model system of early hematopoiesis. Oncogene, 2000. 19(9): p. 1196-205.
21. Rebel, V. I., et al., Distinct roles for CREB-binding protein and p300 in hematopoietic stem cell self-renewal. Proc Natl Acad Sci USA, 2002. 99(23): p. 14789-94.
22. Wilson, A., et al., c-Myc controls the balance between hematopoietic stem cell self-renewal and differentiation. Genes Dev, 2004. 18(22): p. 2747-63.
23. Galan-Caridad, J. M., et al., Zfx controls the self-renewal of embryonic and hematopoietic stem cells. Cell, 2007. 129(2): p. 345-57.
24. Zon, L. I., Intrinsic and extrinsic control of haematopoietic stem-cell self-renewal. Nature, 2008. 453(7193): p. 306-13.
25. Nerlov, C. and T. Graf, PU.1 induces myeloid lineage commitment in multipotent hematopoietic progenitors. Genes Dev, 1998. 12(15): p. 2403-12.
26. Nerlov, C., et al., GATA-1 interacts with the myeloid PU.1 transcription factor and represses PU.1-dependent transcription. Blood, 2000. 95(8): p. 2543-51.
27. Lapidot, T., et al., A cell initiating human acute myeloid leukaemia after transplantation into SCID mice. Nature, 1994. 367(6464): p. 645-8.
28. Blair, A., D. E. Hogge, and H. J. Sutherland, Most acute myeloid leukemia progenitor cells with long-term proliferative ability in vitro and in vivo have the phenotype CD34(+)/CD71(−)/HLA-DR. Blood, 1998. 92(11): p. 4325-35.
29. de Lima, M., et al., Implications of potential cure in acute myelogenous leukemia: development of subsequent cancer and return to work. Blood, 1997. 90(12): p. 4719-24.

All references listed herein are expressly incorporated by reference in their entireties. The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

The invention claimed is:

1. A method for identifying compounds that can modulate the function of NR2F6 in mammalian cells comprising the steps of:
   (i) Expressing in a cellular or cell-free system proteins encoded by one or more recombinant DNA vectors that comprises a ligand binding assay system, having a portion of the cDNA with SEQ ID NO:1
   (ii) Selecting a molecule that can be used as a known ligand, that has been predetermined to bind to the recombinant protein generated by the DNA vectors used in step (i) to generate an amino acid sequence of at least 75% sequence identity to a portion of the amino acid sequence of SEQ ID NO:3
   (iii) Labeling the known ligand using radioactive or non-radioactive methods; or leaving the known ligand unlabeled if detection is performed using the label-free variant of the ligand binding assay
   (iv) Measure the ability of the known ligand to bind to the recombinant protein expressed in step (i)
   (v) Contacting the ligand binding assay with a candidate test compound
   (vi) Measure the ability of the known ligand to bind to the recombinant protein expressed in step (i) while in the presence of test compound
   (vii) Determine the ability of the candidate test compound to bind to the recombinant protein expressed in step (i) by measuring displacement of the known ligand.

2. The method of claim 1 where the recombinant DNA vectors generate protein that is isolated from *Escherichia coli*.

3. The method of claim 1 where the molecule used as the known ligand has been predetermined to bind to the ligand-binding domain of NR2F6.

4. The method of claim 1 wherein the molecule used as the known ligand is troglitazone.

5. The method of claim 1 where the molecule used as the known ligand has been predetermined to bind to an allosteric site on the protein NR2F6.

6. The method of claim 1 where the labeling of the known ligand or protein is enzymatic.

7. The method of claim 1 where the labeling of the known ligand or protein is fluorescent.

8. The method of claim 7 where the fluorescently labeled ligand is used in the method or variant of one of more of the following: fluorescence polarization (FP), fluorescence resonance energy transfer (FRET), fluorescence anisotropy, fluorescence correlation spectroscopy, or time-resolved fluorescence.

9. The method of claim 1 where the labeling of the known ligand or protein is radiolabelled.

10. The method of claim 9 where the radiolabeled ligand is used in the method or variant of scintillation proximity assay (SPA), radioligand binding filtration assay, Flashplate type of assay, ScreenReady type of assay or other suitable detection formation.

11. The method of claim 9 where the labeling of the known ligand or protein is radiolabelled using 3H.

12. The method of claim 9 where the labeling of the known ligand or protein is radiolabelled using 125I.

13. The method of claim 1 where displacement is measured by comparing the binding of the known ligand without test compound to the binding of the known ligand after addition of the test compound.

14. The method of claim 1 wherein a label free format is used to quantify binding in the ligand binding assay.

15. The method of claim 14 where the ability of the test ligand to bind recombinant protein is measured in a non-radioactive way using the change in the angle of polarized light to reflect from a surface on to which ligand or protein has been immobilized.

16. The method of claim 14 where quantification of binding of the known ligand, allowing deduction of binding of the unknown ligand, is performed using one of more of the following: Surface plasmon resonance (SPR), Plasmon-waveguide resonance (PWR), SPR imaging for affinity-based biosensors, Whispering gallery microresonator (WGM), Resonant waveguide grating (RWG), Biolayer Interferometry Biosensor (BIB).

* * * * *

```
                     SEQUENCE LISTING

<160> NUMBER OF SEQ ID NOS: 22

<210> SEQ ID NO 1
<211> LENGTH: 1804
<212> TYPE: DNA
```

<213> ORGANISM: Homo sapiens

<400> SEQUENCE: 1

| | |
|---|---|
| gtgcagcccg tgcccccgc gcgccggggc cgaatgcgcg ccgcgtaggg tccccggggc | 60 |
| cgagaggggt gcccggaggg aagagcgcgg tgggggcgcc ccggcccgc tgccctgggg | 120 |
| ctatggccat ggtgaccggc ggctggggcg gccccggcgg cgacacgaac ggcgtggaca | 180 |
| aggcgggcgg ctacccgcgc gcggccgagg acgactcggc ctcgcccccc ggtgccgcca | 240 |
| gcgacgccga gccgggcgac gaggagcggc cggggctgca ggtggactgc gtggtgtgcg | 300 |
| gggacaagtc gagcggcaag cattacggtg tcttcacctg cgagggctgc aagagctttt | 360 |
| tcaagcgaag catccgccgc aacctcagct acacctgccg gtccaaccgt gactgccaga | 420 |
| tcgaccagca ccaccggaac cagtgccagt actgccgtct caagaagtgc ttccgggtgg | 480 |
| gcatgaggaa ggaggcggtg cagcgcggcc gcatcccgca ctcgctgcct ggtgccgtgg | 540 |
| ccgcctcctc gggcagcccc cgggctcggc cgctggcggc agtggcgagc ggcggagacc | 600 |
| tcttcccggg gcagccggtg tccgaactga tcgcgcagct gctgcgcgct gagccctacc | 660 |
| ctgcggcggc cggacgcttc ggcgcagggg gcggcgcggc gggcgcggtg ctgggcatcg | 720 |
| acaacgtgtg cgagctggcg gcgcggctgc tcttcagcac cgtggagtgg gcgcgccacg | 780 |
| cgcccttctt ccccgagctg ccggtggccg accaggtggc gctgctgcgc ctgagctgga | 840 |
| gcgagctctt cgtgctgaac gcggcgcagg cggcgctgcc cctgcacacg cgccgctac | 900 |
| tggccgccgc cggcctccac gccgcgccta tggccgccga gcgcgccgtg gctttcatgg | 960 |
| accaggtgcg cgccttccag gagcaggtgg acaagctggg ccgcctgcag gtcgactcgg | 1020 |
| ccgagtatgg ctgcctcaag gccatcgcgc tcttcacgcc cgacgcctgt ggcctctcag | 1080 |
| acccggccca cgttgagagc ctgcaggaga aggcgcaggt ggccctcacc gagtatgtgc | 1140 |
| gggcgcagta cccgtcccag ccccagcgct cgggcgcct gctgctgcgg ctccccgccc | 1200 |
| tgcgcgcggt ccctgcctcc ctcatctccc agctgttctt catgcgcctg gtggggaaga | 1260 |
| cgcccattga cactgatc agagacatgc tgctgtcggg gagtaccttc aactggccct | 1320 |
| acggctcggg ccagtgacca tgacggggcc acgtgtgctg tggccaggcc tgcagacaga | 1380 |
| cctcaaggga cagggaatgc tgaggcctcg aggggcctcc cggggcccag gactctggct | 1440 |
| tctctcctca gacttctatt ttttaaagac tgtgaaatgt ttgtcttttc tgttttttaa | 1500 |
| atgatcatga aaccaaaaag agactgatca tccaggcctc agcctcatcc tccccaggac | 1560 |
| ccctgtccag gatggagggt ccaatcctag gacagccttg ttcctcagca ccctagcat | 1620 |
| gaacttgtgg gatggtgggg ttggcttccc tggcatgatg gacaaaggcc tggcgtcggc | 1680 |
| cagagggggct gctccagtgg gcaggggtag ctagcgtgtg ccaggcagat cctctggaca | 1740 |
| cgtaacctat gtcagacact acatgatgac tcaaggccaa taataaagac atttcctacc | 1800 |
| tgca | 1804 |

<210> SEQ ID NO 2
<211> LENGTH: 2218
<212> TYPE: DNA
<213> ORGANISM: Mus musculus

<400> SEQUENCE: 2

| | |
|---|---|
| ggcgccgatg gaacgcgggt gtcaggccgg ccgcagcgcg gggccggcgg cgagcgccag | 60 |
| ggcgaggcca aggctcgggc ccaggcgcag gccgaggccg ccgcgcgag cgctcggcgg | 120 |
| ggagacgatc cagggaaggc cgcgggtcgc actctccact cagctctatc gcctggacct | 180 |

```
ctgcgattac ggccgggcgc gcgcggcgtg cgggactccg ggtctccgac gcgcgctccc      240 gccgccccctc ccccctcgcc gcgtaacttg cggccaaagt ttcccccccgg gctcgggggc    300 gcccgcgcgc gctcggatgg tgagccacta agttggcctg gcggcgggg ccgggccatg      360 gcccccgcga cgctaccggg tcccaggac tccggaccac gggacctggg cgccccagac      420
tcgcgcctct agcgcgcccc cgtcgaccgc gggcacgcgt gggaaagttg gcctggaacc     480
ggcccgacca gttcctgcct ggcgcgcgga ccggccgcag gaagttgccg caaaactttt    540
ttcagggggg tgtgcgaccg gagccccccg agagcgcggg ctgcatgcgc ccggggtagc   600
cgggtccctc tcgggtcgcc aggcgtgccc agaggggacg gactcgtccc ggggcgtacc    660
ggccccgctg tctccggggc tatggccatg gtgaccggtg gctggggcga ccccggaggc   720
gacacgaacg gcgtggacaa ggctggtggg agctacccac gcgcgaccga ggacgattcg    780
gcgtcacctc ccggggcgac cagcgacgcg gagccgggcg acgaggagcg tccggggttg    840
caggtggact gcgtggtgtg cggggacaag tccagtggaa agcattacgg cgtgttcacc    900
tgcgagggct gcaagagttt cttcaagcgc agcatccgcc gcaatctcag ctacacctgc   960
cggtccaacc gtgactgtca gattgatcag caccaccgga accagtgtca gtactgtcgg  1020
ctcaagaagt gcttccgggt gggcatgcgc aaggaggccg tgcagcgagg ccgcatcccg   1080
catgcgctcc ccggtccagc ggcctgcagt ccccgggcg cgacgggcgt cgaacctttc   1140
acggggccgc cagtgtccga gctgattgcg cagctgctgc gtgctgagcc ctacccgcg   1200 gccgacgcct tggtggcgg cggcgctgta ctgggcatcg acaacgtgtg cgagttggcg   1260
gcacgcctgc tgttcagcac ggtcgagtgg gcccgccacg cgcccttctt ccccgagctg   1320
ccggccgccg accaggtggc gctgctgcgc ctcagctgga gtgagctctt cgtgctgaac   1380
gcggcgcagg cggcgctgcc gctgcatacg gcaccgctgc tggccgccgc ggggttgcat  1440
gccgcgccca tggcagccga gcgggccgtg gccttcatgg accaggtgcg tgccttccag  1500
gagcaggtgg acaagctggg ccgcctgcag gtggatgctg cggagtacgg ctgcctcaag  1560
gccatcgcgc tcttcacgcc tgatgcctgt ggccttttctg acccagccca tgtggagagc  1620
ctgcaggaga aggcacaggt ggccctcacc gagtatgtgc gtgcccagta cccatcgcag  1680
ccccagcgct ttgggcgtct gctgctgcgg ctgccagccc tgcgtgctgt gcccgcatcc  1740
ctcatctccc agctcttctt catgcgcctg tgggcaagaa cacccatcga ccctcatc    1800 cgggacatgc ttctgtcagg gagcaccttt aactggccct atggctcggg ctagtgatag  1860
tcaccttcca ggacatacat ggaaactggg gccttgtggg gaccctgggg atcagggccc  1920
cagcttctct tttgagactg atttcttttt ttaaagactg tgaaatgttt gttttgtttt   1980 atttttaaa taatcatgaa accaaaaaga tttggatctc ccaggccttg tcctggcaga   2040
ccttcaacag tctggagcca gcatgctgat gcctctggtg tcatgggtat ctggaaaggc  2100
cactgcagct aggcaggagt actatgggcc aggaggatcc cctggataca tggtccacgg  2160
agggcaccat gggatgatga aaacctggcc aataataaag gtattccctt acttggtc    2218
```

<210> SEQ ID NO 3
<211> LENGTH: 404
<212> TYPE: PRT
<213> ORGANISM: Homo sapiens

<400> SEQUENCE: 3

Met Ala Met Val Thr Gly Gly Trp Gly Gly Pro Gly Gly Asp Thr Asn
1               5                   10                  15

Gly Val Asp Lys Ala Gly Gly Tyr Pro Arg Ala Ala Glu Asp Asp Ser
            20              25              30

Ala Ser Pro Pro Gly Ala Ala Ser Asp Ala Glu Pro Gly Asp Glu Glu
        35              40              45

Arg Pro Gly Leu Gln Val Asp Cys Val Val Cys Gly Asp Lys Ser Ser
    50              55              60

Gly Lys His Tyr Gly Val Phe Thr Cys Glu Gly Cys Lys Ser Phe Phe
65              70              75              80

Lys Arg Ser Ile Arg Arg Asn Leu Ser Tyr Thr Cys Arg Ser Asn Arg
                85              90              95

Asp Cys Gln Ile Asp Gln His His Arg Asn Gln Cys Gln Tyr Cys Arg
                100             105             110

Leu Lys Lys Cys Phe Arg Val Gly Met Arg Lys Glu Ala Val Gln Arg
            115             120             125

Gly Arg Ile Pro His Ser Leu Pro Gly Ala Val Ala Ala Ser Ser Gly
        130             135             140

Ser Pro Pro Gly Ser Ala Leu Ala Ala Val Ala Ser Gly Gly Asp Leu
145             150             155             160

Phe Pro Gly Gln Pro Val Ser Glu Leu Ile Ala Gln Leu Leu Arg Ala
                165             170             175

Glu Pro Tyr Pro Ala Ala Ala Gly Arg Phe Gly Ala Gly Gly Gly Ala
            180             185             190

Ala Gly Ala Val Leu Gly Ile Asp Asn Val Cys Glu Leu Ala Ala Arg
        195             200             205

Leu Leu Phe Ser Thr Val Glu Trp Ala Arg His Ala Pro Phe Phe Pro
210             215             220

Glu Leu Pro Val Ala Asp Gln Val Ala Leu Leu Arg Leu Ser Trp Ser
225             230             235             240

Glu Leu Phe Val Leu Asn Ala Ala Gln Ala Ala Leu Pro Leu His Thr
                245             250             255

Ala Pro Leu Leu Ala Ala Ala Gly Leu His Ala Ala Pro Met Ala Ala
            260             265             270

Glu Arg Ala Val Ala Phe Met Asp Gln Val Arg Ala Phe Gln Glu Gln
        275             280             285

Val Asp Lys Leu Gly Arg Leu Gln Val Asp Ser Ala Glu Tyr Gly Cys
290             295             300

Leu Lys Ala Ile Ala Leu Phe Thr Pro Asp Ala Cys Gly Leu Ser Asp
305             310             315             320

Pro Ala His Val Glu Ser Leu Gln Glu Lys Ala Gln Val Ala Leu Thr
                325             330             335

Glu Tyr Val Arg Ala Gln Tyr Pro Ser Gln Pro Gln Arg Phe Gly Arg
            340             345             350

Leu Leu Leu Arg Leu Pro Ala Leu Arg Ala Val Pro Ala Ser Leu Ile
        355             360             365

Ser Gln Leu Phe Phe Met Arg Leu Val Gly Lys Thr Pro Ile Glu Thr
370             375             380

Leu Ile Arg Asp Met Leu Leu Ser Gly Ser Thr Phe Asn Trp Pro Tyr
385             390             395             400

Gly Ser Gly Gln

<210> SEQ ID NO 4
<211> LENGTH: 390
<212> TYPE: PRT

-continued

<213> ORGANISM: Mus musculus

<400> SEQUENCE: 4

```
Met Ala Met Val Thr Gly Gly Trp Gly Asp Pro Gly Gly Asp Thr Asn
1               5                   10                  15
Gly Val Asp Lys Ala Gly Gly Ser Tyr Pro Arg Ala Thr Glu Asp Asp
            20                  25                  30
Ser Ala Ser Pro Pro Gly Ala Thr Ser Asp Ala Glu Pro Gly Asp Glu
        35                  40                  45
Glu Arg Pro Gly Leu Gln Val Asp Cys Val Val Cys Gly Asp Lys Ser
    50                  55                  60
Ser Gly Lys His Tyr Gly Val Phe Thr Cys Glu Gly Cys Lys Ser Phe
65                  70                  75                  80
Phe Lys Arg Ser Ile Arg Arg Asn Leu Ser Tyr Thr Cys Arg Ser Asn
                85                  90                  95
Arg Asp Cys Gln Ile Asp Gln His His Arg Asn Gln Cys Gln Tyr Cys
            100                 105                 110
Arg Leu Lys Lys Cys Phe Arg Val Gly Met Arg Lys Glu Ala Val Gln
        115                 120                 125
Arg Gly Arg Ile Pro His Ala Leu Pro Gly Pro Ala Ala Cys Ser Pro
    130                 135                 140
Pro Gly Ala Thr Gly Val Glu Pro Phe Thr Gly Pro Pro Val Ser Glu
145                 150                 155                 160
Leu Ile Ala Gln Leu Leu Arg Ala Glu Pro Tyr Pro Ala Ala Gly Arg
                165                 170                 175
Phe Gly Gly Gly Ala Val Leu Gly Ile Asp Asn Val Cys Glu Leu
            180                 185                 190
Ala Ala Arg Leu Leu Phe Ser Thr Val Glu Trp Ala Arg His Ala Pro
        195                 200                 205
Phe Phe Pro Glu Leu Pro Ala Ala Asp Gln Val Ala Leu Leu Arg Leu
    210                 215                 220
Ser Trp Ser Glu Leu Phe Val Leu Asn Ala Ala Gln Ala Ala Leu Pro
225                 230                 235                 240
Leu His Thr Ala Pro Leu Leu Ala Ala Gly Leu His Ala Ala Pro
                245                 250                 255
Met Ala Ala Glu Arg Ala Val Ala Phe Met Asp Gln Val Arg Ala Phe
            260                 265                 270
Gln Glu Gln Val Asp Lys Leu Gly Arg Leu Gln Val Asp Ala Ala Glu
        275                 280                 285
Tyr Gly Cys Leu Lys Ala Ile Ala Leu Phe Thr Pro Asp Ala Cys Gly
    290                 295                 300
Leu Ser Asp Pro Ala His Val Glu Ser Leu Gln Glu Lys Ala Gln Val
305                 310                 315                 320
Ala Leu Thr Glu Tyr Val Arg Ala Gln Tyr Pro Ser Gln Pro Gln Arg
                325                 330                 335
Phe Gly Arg Leu Leu Leu Arg Leu Pro Ala Leu Arg Ala Val Pro Ala
            340                 345                 350
Ser Leu Ile Ser Gln Leu Phe Phe Met Arg Leu Val Gly Lys Thr Pro
        355                 360                 365
Ile Glu Thr Leu Ile Arg Asp Met Leu Leu Ser Gly Ser Thr Phe Asn
    370                 375                 380
Trp Pro Tyr Gly Ser Gly
385                 390
```

```
<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: Synthetic
      mus shNR2F6.1 sequence

<400> SEQUENCE: 5
gatccgcatt acggcgtgtt caccttcaag agaggtgaac acgccgtaat gcttttttct      60
agag                                                                  64

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      mus shNR2F6.2 sequence

<400> SEQUENCE: 6
gatccgcaac cgtgactgtc agattaagtt ctctaatctg acagtcacgg ttgttttttc      60
tagag                                                                 65

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Synthetic
      mus shNR2F6.3 sequence

<400> SEQUENCE: 7
gatccgtgtc cgagctgatt gcgcattcaa gagatgcgca atcagctcgg acatttttc       60 tagag                                                                 65

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: Synthetic
      human shNR2F6.1 sequence

<400> SEQUENCE: 8
gatccgcatt acgtgtctt caccttcaag agaggtgaag acaccgtaat gcttttttct       60
agag                                                                  64

<210> SEQ ID NO 9
<211> LENGTH: 65
<212> TYPE: DNA
<213> ORGANISM: Artificial Sequence
<220> FEATURE:
<223> OTHER INFORMATION: Description of Artificial Sequence: Synthetic
      human shNR2F6.2 sequence

<400> SEQUENCE: 9
gatccgcctc tggacacgta acctattcaa gagataggtt acgtgtccag aggttttttc      60
tagag                                                                 65

<210> SEQ ID NO 10
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      Human NR2F6 Fwd primer

<400> SEQUENCE: 10
tctcccagct gttcttcatg c                                            21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Human NR2F6 Rev primer

<400> SEQUENCE: 11
ccagttgaag gtactccccg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Human GAPDH Fwd primer

<400> SEQUENCE: 12
ggcctccaag gagtaagacc                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Human GAPDH Rev primer

<400> SEQUENCE: 13
aggggtctac atggcaactg                                              20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      3' end Mus NR2F6 Fwd primer

<400> SEQUENCE: 14
cctggcagac cttcaacag                                               19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      3' end Mus NR2F6 Revs primer

<400> SEQUENCE: 15
gatcctcctg gcccatagt                                               19

<210> SEQ ID NO 16
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      3' end Mus L32 Fwd primer

<400> SEQUENCE: 16
gccatcagag tcaccaatcc                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      3' end Mus L32 Rev primer

<400> SEQUENCE: 17
aaacatgcac acaagccatc                                                    20

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      human siRNA sequence

<400> SEQUENCE: 18
gccgucucaa gaagugcuu                                                     19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      human siRNA sequence

<400> SEQUENCE: 19
cauugagaca cugaucaga                                                     19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      human siRNA sequence

<400> SEQUENCE: 20
gcaagcauua cggugucuu                                                     19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      human siRNA sequence

<400> SEQUENCE: 21
ccccuagcau gaacuugug                                                     19

<210> SEQ ID NO 22
<211> LENGTH: 232
<212> TYPE: PRT
<213> ORGANISM: Homo sapiens
```

```
<400> SEQUENCE: 22

Leu Leu Arg Ala Glu Pro Tyr Pro Ala Ala Ala Gly Arg Phe Gly Ala
1               5                   10                  15

Gly Gly Gly Ala Ala Gly Ala Val Leu Gly Ile Asp Asn Val Cys Glu
            20              25                  30

Leu Ala Ala Arg Leu Leu Phe Ser Thr Val Glu Trp Ala Arg His Ala
        35              40                  45

Pro Phe Phe Pro Glu Leu Pro Val Ala Asp Gln Val Ala Leu Leu Arg
    50              55                  60

Leu Ser Trp Ser Glu Leu Phe Val Leu Asn Ala Ala Gln Ala Ala Leu
65              70                  75                  80

Pro Leu His Thr Ala Pro Leu Leu Ala Ala Ala Gly Leu His Ala Ala
                85                  90                  95

Pro Met Ala Ala Glu Arg Ala Val Ala Phe Met Asp Gln Val Arg Ala
                100                 105                 110

Phe Gln Glu Gln Val Asp Lys Leu Gly Arg Leu Gln Val Asp Ser Ala
                115                 120                 125

Glu Tyr Gly Cys Leu Lys Ala Ile Ala Leu Phe Thr Pro Asp Ala Cys
    130                 135                 140

Gly Leu Ser Asp Pro Ala His Val Glu Ser Leu Gln Glu Lys Ala Gln
145             150                 155                 160

Val Ala Leu Thr Glu Tyr Val Arg Ala Gln Tyr Pro Ser Gln Pro Gln
                165                 170                 175

Arg Phe Gly Arg Leu Leu Leu Arg Leu Pro Ala Leu Arg Ala Val Pro
                180                 185                 190

Ala Ser Leu Ile Ser Gln Leu Phe Phe Met Arg Leu Val Gly Lys Thr
        195                 200                 205

Pro Ile Glu Thr Leu Ile Arg Asp Met Leu Leu Ser Gly Ser Thr Phe
        210                 215                 220

Asn Trp Pro Tyr Gly Ser Gly Gln
225                 230
```